United States Patent [19]
Miller et al.

[11] Patent Number: 5,830,740
[45] Date of Patent: Nov. 3, 1998

[54] SERINE PROTEASE OPERATIVE BETWEEN 75°C. AND 103°C.

[75] Inventors: Jeffrey H. Miller, Los Angeles; Peter Markiewicz, Santo Monk, both of Calif.; Paul Völkl, Regensburg, Germany

[73] Assignee: Research Corporation Technologies, Inc., Tuscson, Ariz.

[21] Appl. No.: 278,042

[22] Filed: Jul. 20, 1994

[51] Int. Cl.[6] .............................. C12N 9/52; C12N 15/57; C12N 15/70; C11D 3/386
[52] U.S. Cl. ......................... 435/220; 435/219; 435/68.1; 435/69.1; 435/252.3; 435/252.31; 435/252.33; 435/320.4; 435/262; 510/300; 536/23.2
[58] Field of Search ..................................... 435/219, 220, 435/68.1, 69.1, 252.3, 252.31, 252.33, 262; 536/23.2; 510/27, 300

[56] References Cited

U.S. PATENT DOCUMENTS

| | | | |
|---|---|---|---|
| 4,980,288 | 12/1990 | Bryan et al. | 435/222 |
| 4,990,542 | 2/1991 | Bryan et al. | 435/222 |
| 5,215,907 | 6/1993 | Tang et al. | 435/219 |
| 5,346,821 | 9/1994 | Antranikian et al. | 435/220 |
| 5,391,489 | 2/1995 | Kelly et al. | 435/220 |

OTHER PUBLICATIONS

Arnold, F. H., FASEB Journal, vol. 7, "Engineering proteins for nonnatural environments", pp. 744–749, 1993.

Mozhaev, V. V., Trends in Biotechnology, vol. 11, "Mechansm–based strategies for protein thermostablilization", pp. 88–95, 1993.

Goodenough, P. W., et al., Biochemical Society Transactions, vol. 19, "Protein engineering to change thermal stability for food enzymes", pp. 655–662, 1991.

Bell, J. A., et al., in Use of X–Ray Crystallography in the Design of Antiviral Agents, Laver, W. G., and Air, G. M. Eds., Academic Press, Inc., "Approaches to the design of proteins of enhanced thermostability", pp. 233–245, 1990.

Matthews, B. W., et al., Proceedings of the National Academy of Sciences, U.S.A., vol. 84, "Enhanced protein thermostabilityfrom site–directed mutations that decrease the entropy of unfolding", pp. 6663–667, 1987.

Volkl, P., et al., Protein Science, vol. 3, "The sequence of a subtilisin–type protease (aerolysin) from the hyperthermophilic archaeum *Probaculum aerophilum* reveals sites important to thermostability", pp.1329–1340, 1994.

Hirono, I., et al., Microbial pathogenesis, vol. 13, "Nucleotide sequences and characterization of hemolysin genes from *Aeromonas hydrophila* and *Aeromonas sobria*", pp. 433–446, 1992.

Howard, S. P., et al., Journal of Bacteriology, vol. 169, "Nucleotide sequence of the gene for the hole–forming toxin aerolysin of *Aeromonas hydrophila*", pp. 2869–2871, 1987.

Völkl et al., Pyrobaculum Aerophilum SP. Nov., A Novel Nitrate–Reducing Hyperthermophilic Archaeum, *Applied and Environmental Microbiology*, Sep. 1993, pp. 2918–2926.

Siezen et al., Homology Modelling and Protein Engineering Strategy of Subtilases, the Family of Subtilisin–Like Serine Proteinases, *Protein Engineering*, vol. 4, No. 7, pp. 719–737, 1991.

Meloun et al., Complete Primary Structure of Thermitase From Thermoactinomyces Vulgaris and Its Structural Features Related to the Subtilisin–Type Proteinases, *FEBS Letters*, vol. 183, No. 2, Apr. 1985, pp. 195–200.

Thayer, A.M., Biotechnology's Impact on Chemical Processes Only In Its Infancy, Oct. 14, 1991, *C&EN*, pp. 13–14.

Primary Examiner—Robert A. Wax
Assistant Examiner—William W. Moore
Attorney, Agent, or Firm—Scully, Scott, Murphy & Presser

[57] ABSTRACT

A subtilisin which exhibits proteolytic activity at temperatures ranging from 75° C. to 130° C. The subtilisin has been given the name aerolysin because it was initially isolated from the hyperthermophilic archaeum, *Pyrobaculum aerophilum*. The amino acid sequence of aerolysin is disclosed as well as the nucleotide sequence which encodes the enzyme. Aerolysin and related modified enzymes are useful as high temperature detergent additives and, among other things, may be used in combination with a wide variety of other detergent agents.

18 Claims, 14 Drawing Sheets

```
GGAACAAAGCTGAGCTCACgGTGCGCGCTCTAGACTAGTGATCCATTGGCGAGTGACTTGTGAATACTCCAAGCGCtttAC
-162
TTAATCCAGTGGGAGGCAAGCTGACTATTAGACAAGCCCCCAGTACTTCAACGAGTTAGATTTACAATTGAGAATCGGC GCTGAGGTGATAGAAACTGCGAAAAGCATAGGCGTTTCTAAAAAGTTCAAAAAGAGTTTCCGCTGTAATAGACGAATTA
1/1
ATG TCA TAA TAT TTG AAA AGA CGT AAA AAA CTG GCT CAA TGC CAA AGG TTT GGC GGC ACT
 M   S  *(Q)  Y   L   K   R   R   K   K   L   A   Q   C   Q   R   F   G   G   T
61/21                                31/11                            91/31
AGT GGC ATT TCT TCA AGC CGC GAG ATT GTA GTG GGC TAT GTC GAT TCC CCT ACG GAA
 S   G   I   S   S   S   R   E   I   V   V   G   Y   V   D   S   P   T   E
121/41                                151/51
GCT TTA AAA GAG TTA AAT AAA ACA GGC GAT ATT AAA ATA AAA CAT TTA AAA GAA ATC
 A   L   K   E   L   N   K   T   G   D   I   K   I   K   H   L   K   E   I
181/61                                211/71
AAG GCA ATT GTA TTA AAC ATT CCC GAT AAT AAA ACA GAG AAA CTT AAG GAA AAG TTA AAA
 K   A   I   V   L   N   I   P   D   N   K   T   E   K   L   K   E   K   L   K
241/81                                271/91
GGA GTT AGA TAT ATA GAG GAA GAC GGC GTT GCG TAT TTT GGT TTC TCT AAT TAT ACC
 G   V   R   Y   I   E   E   D   G   V   A   Y   F   G   F   S   N   Y   T
301/101                               331/111
GAT GTA CAG TGG AAT GTA AAA ATG ATA AAC GCC CCG CGT CTG GGA CGC CTA TTT TCT GAC
 D   V   Q   W   N   V   K   M   I   N   A   P   R   L   G   R   L   F   S   D
361/121                               391/131
ATT TGG CGA CGC GCA TTT GGC TAT GGA TAT AAA GTG GCG GTG CTC GAC ACA GGC ATT GAC
 I   W   R   R   A   F   G   Y   G   Y   K   V   A   V   L   D   T   G   I   D
421/141                               451/151
TAC AAG CAC CCG GAG CTA TCC GGC AAG AAG TGC GAC AGA GTT TAT TGT ATT AAC GGC AAC ACT
 Y   K   H   P   E   L   S   G   K   K   C   D   R   V   Y   C   I   N   G   N   T
481/161                               511/171
CTC TAC AAG GGG ACA AAT TTA AGG AAG GAC GCC GAC GTT TAT TAT GCC GTT GTG CAC GTA
 L   Y   K   G   T   N   L   R   K   D   A   D   V   Y   Y   A   V   V   H   V
541/181                               571/191
GCT GGG ATA ATA GCC GCT TCG TTG AAT AAC GTG AGC AGC GCA GCC GTT GTG CCT AAG GTG
 A   G   I   I   A   A   S   L   N   N   V   S   S   A   A   V   V   P   K   V
601/201                               631/211
CAG TTA ATA GCA GTT AAG GTC TTA TAC GAC TCC GGG TAC TAT AGC GAT ATT GCC
 Q   L   I   A   V   K   V   L   Y   D   S   G   Y   Y   S   D   I   A
```

FIG. 1

```
661/221
GAG GGG ATA ATA GAG GCA GTT AAA GCA GGG GCT TTA ATT CTA TCA ATG TCC CTA GGA GGC
 E   G   I   I   E   A   V   K   A   G   A   L   I   L   S   M   S   L   G   G
721/241
CCC ACA GAC GCC TCT GTG TTG AGA GAC GCC GCC TCG TAT TGG GCC TAT CAA CAA AAC GGC GCT GTT
 P   T   D   A   S   V   L   R   D   A   A   S   Y   W   A   Y   Q   Q   N   G   A   V
781/261
CAG ATA GCC GCT GGT AAT TCA GGC GAT GGC GAT CCC TTG ACA AAC AAC GTG GGG TAT
 Q   I   A   A   G   N   S   G   D   G   D   P   L   T   N   N   V   G   Y
841/281
CCC GCC AAG TAT AGC TGT GTA ATA GCA GCG GCG GCG GTA GAT CAA CAA AAC GGC TCC GTC CCC
 P   A   K   Y   S   C   V   I   A   A   A   A   V   D   Q   Q   N   G   S   V   P
901/301
ACG TGG AGT AGC GAC GGG CCA GAG GTG GAC ACC GCG GCG CCA GTA AAC ATA TTG TCC
 T   W   S   S   D   G   P   E   V   D   T   A   A   P   V   N   I   L   S
961/321
ACA TAT CCC GGC GGC AGA TAC GCG CAA TAT ATG TCC GGC ACA TCT ATG GCG CCT CAC GTG
 T   Y   P   G   G   R   Y   A   Q   Y   M   S   G   T   S   M   A   P   H   V
1021/341
ACT GGC GTA GCG GCC TTA ATA GTA CAA GCG TTG AGA CTC GCC TCA GGC AAG TTG CTA ACC
 T   G   V   A   A   L   I   V   Q   A   L   R   L   A   S   G   K   L   L   T
1081/361
CCA GAC GAG GTT TAT CAA GTA ATT ACC TCT ACG GCT AAG GAT ATC GGC CCG CCC GGT TTT
 P   D   E   V   Y   Q   V   I   T   S   T   A   K   D   I   G   P   P   G   F
1141/381
GAC GTC TTT TCG GGC TAC GGC TTA GTT GAC GCA TAC GCC GCA GTT GTG GCC GCG CTA AGT
 D   V   F   S   G   Y   G   L   V   D   A   Y   A   A   V   V   A   A   L   S
1201/401
CGC TAA CTTTTTATATAGAATTCAAATTGAGTATGCCCAGTGGACTGAGTACATACTCTATAAAAATTGGGAA
 R   *
AACTCCGTCGCCAGGTGACGTCGTTGAAATAGTTCCAGATCTCGTCGGCTTTCAGACTTGACGGGTACCACGTCCTTG

AGGTGTTGGAAAGCATGGGCAAAGTGGAGGTGTTTGACAGGGAGAGTCGTTGTTGCGTTTGATCACTTGTCCCGCCC

CCAAATCAGAGAGCCGCTGAGATAATGGTGTACATAAGGCGTCATGTCAAGGCTCTGAAGGCTTCCTAATTTCTACGACGTA

GGCGCGGCCATTTTGCACCAGATTATCTGGAGAAATACGCCTTGCCGGGCCAAGTGATCTTCGCCGGATAGCCACACTTT

CACCGCC
```

FIG.2

```
                    10                  20                  30                  40                  50
AEROLYSIN           YIEEDGVAYAFGFSNYTD-VQWNVKMINAPASGTLFSHIWRRAF-GYGVKVAVLDT
THERMITASE          ------YTPNDPYFSSRQYGPQKIQAPQA-------WDIA-EGSGAKIAIVDT
Halolysin           DVEYAEDNATYEAIATPNDPQYGQQYAPQQVNCEAA----WDVTYGDPGVTISVVDQ
SUBT. TA41          TNKPEALYNAMA---ASQSTPWGIKAIYNNSN-------LTSTSGGAGINIAVLDT
SUBT. CARLSBERG     YVEEDHVAHALAL---AQTVPYGIPLIKADKV-------QAQGFKGANVKVAVLD
SUBT. BACMS         YVEEDHIAHEY-----AQSVPYGISQIKAPAL-------HSQGYTGSNVKVAVID
SUBT. I168          YVEEDHIAHEY-----AQSVPYGISQIKAPAL-------HSQGYTGSNVKVAVID
SUBT. J             YVEEDHIAHEY-----AQSVPYGISQIKAPAL-------HSQGYTGSNVKVAVID
SUBT. DY            ---------------AQTVPYGIPLIKADKV-------QAQGYKGANVKVGIIDT
SUBT. BPN'          YVEEDHVAHAY-----AQSVPYGVSQIKAPAL-------HSQGYTGSNVKVAVID
ISP-I               ---------------DVNELPEGIKVIKA-------PEMWAKGVKGKNIKVAVLDT
B. ALCALOPHILUS     YIEEDAEVTTM-----AQSVPWGISRVQAPAA-------HNRGLTGSGVKVAVLD
ELASTASE YAB        YIEEDAEVTTM-----QTVPWGINRVQAPIA-------QSRGFTGTGVRVAVLD
BSUB MINOR PROT.    FTAADSTDFKVLSDGTDTSDNFEQWNLEPIQVKQA----WKAGLTGKNIKIAVIDS
Aqualysin I         FIEADKVVRAW-----ATQSPAPWGLDRIDQRDLPLSNSYTY--TATGRGVNVYVID
PTOTEINASE K        YIEQDAVVTIN-----AAQTNAPWGLARISSTSPGTSTYYY--DESAGQGSCVYVID
PredictProtein      eee hhhhhhE     LLL L              LLL eee L LL eEEEEEE
Thermitase 2°       THHHHTHHHHHHHTTHHHHT           TT        TT TT EEEEEE
Proteinase K 2°                EETT HHHHHHT              EE TTTTT TT EEEEEE
Carlsberg 2°             THHHHHTHHHH                        HHHT    TT TT EEEEEE
BPN' 2°                  HHHHHHTTHHHHH                      TT        TT TT EEEEEE
```

```
                             110              120              130              140
AEROLYSIN            LNNVSAAGVVPKVQLIAVKVLYD-SGSGYYSDIAEGIIEAVKAGAL
THERMITASE           NNSTGIAGTAPKASILAVRVL-DNSGSGTWTAVANGITYAADQGAK
Halolysin            NNATGHAGIS-NCSLLSARAL-GDGGGGSLTDIADAIQWSADQGAD
SUBT. TA41           GTGSGVYGVAPEADLWAYKVL-GDDGSGYADDIAEAIRHAGDQATA
SUBT. CARLSBERG      DNTTGVLGVAPSVSLYAVKVL-NSSGSGTYSGIVSGIEWATTNGMD
SUBT. BACMS          NNSIGVLGVAPSSALYAVKVL-DSTGSGQYSWIINGIEWAISNNMD
SUBT. I168           NNSIGVLGVSPSASLYAVKVL-DSTGSGQYSWIINGIEWAISNNMD
SUBT. J              NNSIGVLGVSPSASLYAVKVL-DSTGSGQYSWIINGIEWAISNNMD
SUBT. DY             DNTTGVLGVAPNVSLYAIKVL-NSSGSGTYSAIVSGIEWATQNGLD
SUBT. BPN'           NNSIGVLGVAPSASLYAVKVL-GADGSGQYSWIINGIEWAIANNMD
ISP-I                DSNGGIAGVAPEASLLIVKVLGGENGSGQYEWIINGINYAVEQKVD
B. ALCALOPHILUS      NNSIGVLGVAPNAELYAVKVL-GASGSGSVSSIAQGLEWAGNNGMH
ELASTASE YAB         NNSIGVLGVAPNVDLYGVKVL-GASGSGSISGIAQGLQWAANNGMH
BSUB MINOR PROT.     HNGYGIDGIAPEAQIYAVKAL-DQNGSGDLQSLLQGIDWSIANRMD
Aqualysin I          --TYGVA---KAVNLYAVRVL-DCNGSGSTSGVIAGVDWVTRNHRR
PROTEINASE K         --TYGVA---KKTQLFGVKVL-DDNGSGQYSTIIAGMDFVASDKNN
PredictProtein       LLLeeee         eEEEEEE           LLL   hhhhhhhhhLLL
Thermitase 2°           T            TT EEEEEE        TT E  HHHHHHHHHHHHHTT
Proteinase K 2°       T               TT EEEEEE       TT    HHHHHHHHHHHHHHH
Carlsberg 2°                          TT EEEEEE       TT E  HHHHHHHHHHHHHTT
BPN' 2°                               TT EEEEEE       TT    HHHHHHHHHHHHHTT
```

FIG. 6C

```
                          150         160         170         180         190         200
AEROLYSIN         -------ILSMSLGGPRDASVLRDASYWAYQQGAVQIAAAGNSGDGDPLTNNVGYPAKYSCV
THERMITASE        -------VISLSLGGTVGNSGLQQAVNYAWNKGSVVVAAAGNAG----NTAPNYPAYYSNA
Halolysin         -------VINMSLGGGGFSQTLSNACEYAYNQGSLLVAAAGN-----GYGNSVSYPAAYDTV
SUBT. TA41        ---LNTKVVINMSLGSSGESSLITNAVDYAYDKGVLIIAAAGNSGPKPGSIGYPGALVNAVAV
SUBT. CARLSBERG   -------VINMSLGGPSGSTAMKQAVDNAYARGVVVAAAGNSGSSGN-TNTIGYPAKYDSV
SUBT. BACMS       -------VINMSLGGPTGSTALKTVVDKAVSSGIVVAAAAGNEGSSGS-TSTVGYPAKYPST
SUBT. I168        -------VINMSLGGPTGSTALKTVVDKAVSSGIVVAAAAGNEGSSGS-TSTVGYPAKYPST
SUBT. J           -------VINMSLGGPSGSTALKTVVDKAVSSGIVVAAAAGNEGSSGS-SSTVGYPAKYPST
SUBT. DY          -------VINMSLGGPSGSTALKQAVDKAYASGIVVAAAGNSGSSGS-QNTIGYPAKYDSV
SUBT. BPN'        -------VINMSLGGPSGSAALKAAVDKAVASGVVVAAAGNEGTSGS-SSTVGYPGKYPSV
ISP-I             -------IISMSLGGPSDVPELEEAVKNAVKNGVLVVCAAGNEGDGDERTEELSYPAAYNEV
B. ALCALOPHILUS   -------VANLSLGSPSPSATLEQAVNSATSRGVLVVAASGNSG-----AGSISYPARYANA
ELASTASE YAB      -------IANMSLGSSAGSATMEQAVNQATASGVLVVAASGNSG-----AGNVGFPARYANA
BSUB MINOR PROT.  -------IVNMSLGTTSDSKILHDAVNKAYEQGVLLVAASGNDG----NGKPVNYPAAYSSV
Aqualysin I       ----PAVANMSLGGGV-STALDNAVKNSIAAGVVYAVAAGNDNANACNYS----PARVAEA
PROTEINASE K      RNCPKGVVASLSLGGGY-SSSVNSAAARLQSSGVMVAVAAGNNNADARNYS----PASEPSV
PredictProtein    EEEEEeLLLL hhHHHHHHHHhh LL EEEEEe LLLLLLLLLL          L
Thermitase 2°     EEEE  EEE           HHHHHHHHHHHHHHT  EEEEE           EHHHEE   ETT  TT
Proteinase K 2°   H    TT EEEEE  EE    HHHHHHHHHHHHHHHT EEEEE                    TTT  TT
Carlsberg 2°      EEEE  EEE           HHHHHHHHHHHHHHT  EEEEE                    TT   TT
BPN' 2°           EEEE  E             HHHHHHHHHHHHHHHT EEEEE                    ETTT TT
```

FIG.6D

```
                          210        220        230        240        250
AEROLYSIN         IAAAAVDQNGSVPTWSSDGPEVDTAAPGVNILSTYPGGR---------YAYMSGTSMA
THERMITASE        IAVASTDQNDNKSSFSTYGSVVDVAAPGSWIYSTYPTST---------YASLSGTSMA
Halolysin         MAVSSLDEGETLSAFSNLGPEIELAAPGGNVLSSIPWDN---------YDTFSGTSMA
SUBT. TA41        AALENTIQNGTYRVADFSSRGHKRTAGDYVIQKGDVEISAPGAAVYSTWFDGGYATISGTSMA
SUBT. CARLSBERG   IAVGAVDSNSNRASFSSVGAELEVMAPGAGVYSTYPTST---------YATLNGTSMA
SUBT. BACMS       IAVGAVNSANQRASFSSSAGSELDVMAPGVSIQSTLPGGT---------YGAYNGTSMA
SUBT. I168        IAVGAVNSSNQRASFSSSAGSELDVMAPGVSIQSTLPGGT---------YGAYNGTSMA
SUBT. J           IAVGAVNSSNQRASFSSSAGSELDVMAPGVSIQSTLPGGT---------YGAYNGTSMA
SUBT. DY          IAVGAVDSNKNRASFSSVGAELEVMAPGVSVYSTYPSNT---------YTSLNGTSMA
SUBT. BPN'        IAVGAVDSSNQRASFSSVGPELDVMAPGVSIQSTLPGNK---------YGAYNGTSMA
ISP-I             IAVGSVSVARELSEFSNANKEIDLVAPGENILSTLPNKK---------YGKLTGTSMA
B. ALCALOPHILUS   MAVGATDQNNNRASFSQYGAGLDIVAPGVNVQSTYPGST---------YASLNGTSMA
ELASTASE YAB      MAVGATDQNNNRATFSQYGAGLDIVAPGVQSTVPGNG-----------YASFNGTSMA
BSUB MINOR PROT.  VAVSATNEKNQLASFSTTGDEVEFSAPGTNITSTYLNQY---------YATGSGTSMA
Aqualysin I       LTVGATTSSDARASFSNYGSCVDLFAPGASIPSAWYTSDTAT------QTLNGTSQA
PROTEINASE K      CTVGASDRYDRRSSFSNYGSVLDIFGPGTSILSTWIGGSTRS------ISGTSMA
PredictProtein    EEE  LLLL       LLL  eeEee L        eeEee          eee
Thermitase 2°     EEEEEE TT    E TT    TT  EEEE        EEEEETTTE      EEEE EHHH
Halolysin 2°      EEEEEE TT EE E TT    E TT   EEEE    EEEEETTTEEEE        E  HHH
Proteinase K 2°   EEEEEE TT    E TT    TT  EEEE        EEEEETTTE      EEEE HHH
Carlsberg 2°      EEEEEE TT    E TT    TT  EEEE        EEEEETTTE
BPN' 2°           EEEEEE TT    E TT    TT  EEEE        EEEEETTTE      EEEE HHH

FIG. 7A
```

```
                        260              270              280              290
AEROLYSIN               TPHVTGVAALIQALRLASGKRLLTPDEVYQVITSTAKDIGPPGFD
THERMITASE              TPHVAGVAGLLASQGRS--------ASNIRAAIENTADKISGTGT-
Halolysin               SPVVAGVAGFTLSAHPN--------LSNAELRSHLQNTAVDVGLSSEE
SUBT. TA41              SPHAAGLAAKIWAQSPA--------ASNVDVRGELQTRASVN-DILSG
SUBT. CARLSBERG         SPHVAGAAAALILSKHPN--------LSASQVRNRLSSTATYLGSSF--
SUBT. BACMS             TPHVAGAAAALILSKHPT--------WTNAQVRDRLESTATYLGSSF--
SUBT. I168              TPHVAGAAAALILSKHPT--------WTNAQVRDRLESTATYLGNSF--
SUBT. J                 TPHVAGAAAALILSKHPT--------WTNAQVRDRLESTATYLGNSF--
SUBT. DY                SPHVAGAAAALILSKYPT--------LSASQVRNRLSSTATNLGDSF--
SUBT. BPN'              SPHVAGAAAALILSKHPN--------WTNTQVRSSLENTTTKLGDSF--
ISP-I                   APHVSGALALIKSYEEESFQRK--LSESEVFAQLIRRTLPLDIAK
B. ALCALOPHILUS         TPHVAGAAAALVKQKNPS--------WSNVQIRNHLKNTATSLGSTN--
ELASTASE YAB            TPHVAGVAALVKQKNPS--------ESNVQIRNHLKNTATNLGNTT--
BSUB MINOR PROT.        TPHAAAMFALLKQRDPA--------ETNVQLREEMRKNIVDLGTAGRD
Aqualysin I             TPHVAGVAALYLEQNP--------SATPASVASAILNGATTGRLS--
PROTEINASE K            TPHVAGLAAYLM--------TLGKTTAASACRYIADTANKGDLS-N
PredictProtein          hhhhhhhhhhhh  LLLLLL hhhhhhhhhh         LLLL
Thermitase 2°           HHHHHHHHHHHH HHTTT            HHHHHHHHT E TTET
Proteinase K 2°         HHHHHHHHHHHHH       TT  TTTHHHHHHT EE     E
Carlsberg 2°            HHHHHHHHHHHHHHH TT   HHHHHHHHHT E        HH
BPN' 2°                 HHHHHHHHHHHHHHH T    HHHHHHHHHTT E       HH
```

FIG. 7B

| | 300 310 | |
|---|---|---|
| AEROLYSIN | VFSGYGLVDAYAAVVAALSR* | 100 |
| THERMITASE | -YWAKGRVNAYKAVQY* | 43 |
| Halolysin | Q--GHGRVDAGQAVTTDPGDG**** | 32 |
| SUBT.TA41 | NSAGSGDDIASGFGFAKVQ* | 31 |
| SUBT. CARLSBERG | -YYGKGLINVEAAAQ* | 46 |
| SUBT. BACMS | -YYGKGLINVQAAAQ* | 44 |
| SUBT. I168 | -YYGKGLINVQAAAQ* | 43 |
| SUBT. J | -YYGKGLINVQAAAQ* | 43 |
| SUBT. DY | -YYGKGLINVEAAAQ* | 43 |
| SUBT. BPN' | -YYGKGLINVQAAAQ* | 43 |
| ISP-I | TLAGNGFLYLTAPDELAEKAEQSHLLTL* | 38 |
| B. ALCALOPHILUS | -LYGSGLVNAEAATR* | 43 |
| ELASTASE YAB | -QFGSGLVNAEAATR* | 42 |
| BSUB MINOR PROT. | QQFGYGLIQYKAQATD***** | 34 |
| Aqualysin I | -GIGSGSPNRLLYSLLSSGSG* | 31 |
| PROTEINASE K | IPFGTVNLLAYNNYQA* | 33 |
| PredictProtein | hhhHHHHHHHHh L | |
| Thermitase 2° | TTE E HHHHHT | |
| Proteinase K 2° | TT EE | |
| Carlsberg 2° | HHTT E HHHHT | |
| BPN' 2° | HHTT E HHHHT | |

FIG.7C

SERINE PROTEASE OPERATIVE BETWEEN 75°C. AND 103°C.

This invention was made with Government support under Navy Grant No. N00014-92-J-1403. The Government has certain rights in the invention.

BACKGROUND OF THE INVENTION

1. Field of the Invention

The present invention relates generally to serine proteases which retain activity at relatively high temperatures. More particularly, the present invention relates to the isolation and identification of a new subtilisin-type protease which exhibits proteolytic activity at temperatures ranging from about 75° C. up to about 130° C.

2. Description of Related Art

The publications and other reference materials referred to herein to describe the background of the invention and provide additional detail regarding its practice are hereby incorporated by reference. For convenience, the reference materials are numerically referenced and grouped in the appended bibliography.

Subtilisins are a family of extracellular serine proteases. Although numerous different families of serine proteases exist, subtilisins and chymotrypsin are the two groups of enzymes which have received the most attention. Subtilisins have been used widely in the food processing and laundry industry. For example, subtilisins are commonly used in detergents because of their ability to remove protein-based stains. Subtilisins are also widely used in organic synthesis.

In recent years, many new subtilisin-like serine proteases have been isolated from archaea, bacteria, fungi, yeasts and higher eukaryotes (1). The three dimensional structure and amino acid sequence of a number of these proteases have been established. For example, the following subtilisins have been characterized: BPN'/Novo from Bacillus amyloliquefaciens; Carlsberg from B. licheniformins; thermitase from Thermoactinomyces vulgaris; proteinase K from Tritirachium.

In view of their commercial importance, the subtilisins have been studied and engineered extensively. Attempts to produce subtilisins which are stable at relatively high temperatures have received particular attention because of their potential for use in conventional laundry operations where detergents are commonly subjected to temperatures approaching 100° C. or higher. U.S. Pat. Nos. 4,980,288 and 4,990,552 describe thermally stable subtilisins and methods for modifying the subtilisins in order to achieve maximum thermal stability. A number of other researchers have engineered amino acid substitutions into naturally occurring subtilisins in order to increase their thermal stability. For example, Pantoliano et al. (4) made six concerted amino acid substitutions in subtilisin BPN', causing near additive increases in thermal stability. The $T_m$ for the protein was changed from 58.5° C. to 72.8° C. In another study (5), three mutations were made in the aprA gene of B. subtilis to increase its long-term stability. Two of these mutations replaced asparagine residues with serines which resulted in the prevention of cyclization with adjacent glycine residues. A third substitution changed asparagine in the high affinity $Ca^{++}$ binding pocket to aspartic acid. These changes resulted in a significantly higher unfolding temperature and increased detergent resistance. Eijsink et al. (6) increased the stability of a neutral protease by removing charged residues at the N-terminus of alpha helices. More recently, Chen and Arnold (2) used sequential random mutagenesis to select a mutant subtilisin E which was able to function in 60% dimethyl formamide. The 10 effective mutations clustered in variable loop regions on one side of the protein.

The above exemplary investigations have focused on proteases which are easily grown and then modified in an attempt to achieve high temperature stability. However, the majority of the engineered proteases have displayed disappointing stability at temperatures much above 80° C. Accordingly, there is a continuing need to isolate and identify new serine proteases which are stable at the temperatures required for many laundry operations and other high temperature processes where proteolytic activity is required.

SUMMARY OF THE INVENTION

In accordance with the present invention, a new subtilisin-type serine protease has been discovered which exhibits proteolytic activity at temperatures ranging from about 75° C. up to about 130° C. This new subtilisin was initially isolated from a homogenate of *Pyrobaculum aerophilum* and has been given the name "aerolysin". Aerolysin is located principally in the cell envelope with a smaller amount being located in the cytoplasm.

Aerolysin, and thermally stable modifications thereof, may be used in the same type of applications in which other high temperature subtilisins have been successfully employed. The high temperature proteolytic activity of aerolysin is especially well-suited for use as a detergent additive. Aerolysin will also find use in a wide variety of other situations where its high temperature proteolytic activity will be of value.

As a feature of the present invention, the entire DNA sequence of the gene which encodes aerolysin has been determined as well as the entire amino acid sequence of the enzyme. Accordingly, aerolysin may be expressed in large quantities in organisms which have been genetically engineered to include the aerolysin gene.

The above described and many other features and attendant advantages of the present invention will become better understood by reference to the following detailed description when taken in conjunction with the accompanying drawings.

BRIEF DESCRIPTION OF THE DRAWINGS

The file of this patent contains at least one drawing executed in color.

FIGS. 1 and 2 set forth the nucleotide sequence and corresponding amino acid sequence for aerolysin. The predicted leader and "prepro" sequences have been underlined.

Shaded regions indicate sites that may be in close proximity in the tertiary structure.

Figure 4:
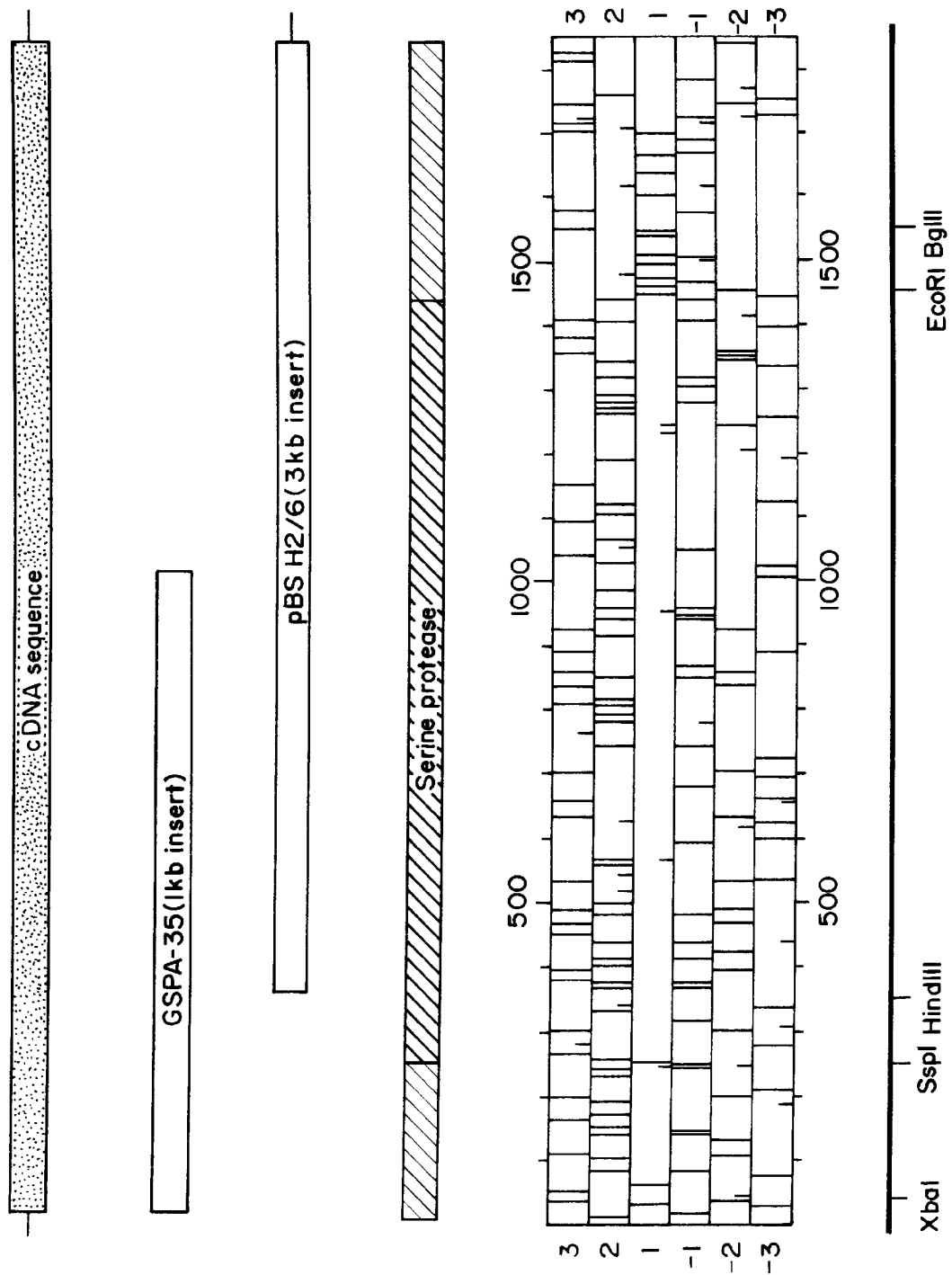

FIG. 4 is a schematic diagram of the aerolysin gene from *Pyrobaculum aerophilum* including: (a) the clones used to construct the total sequence containing the aerolysin gene (ESUB3: cDNA clone obtained by plaque lift hybridization of poly-A primed cDNA library. GSPA 35: randomly sequenced clone of genomic 1–2 kb library. pBH2/6: Hind III fragment obtained by Southern Blot and colony lift hybridization); (b) the open reading frame (+1) encoding aerolysin; and (c) the restriction map.

Figure 5A:
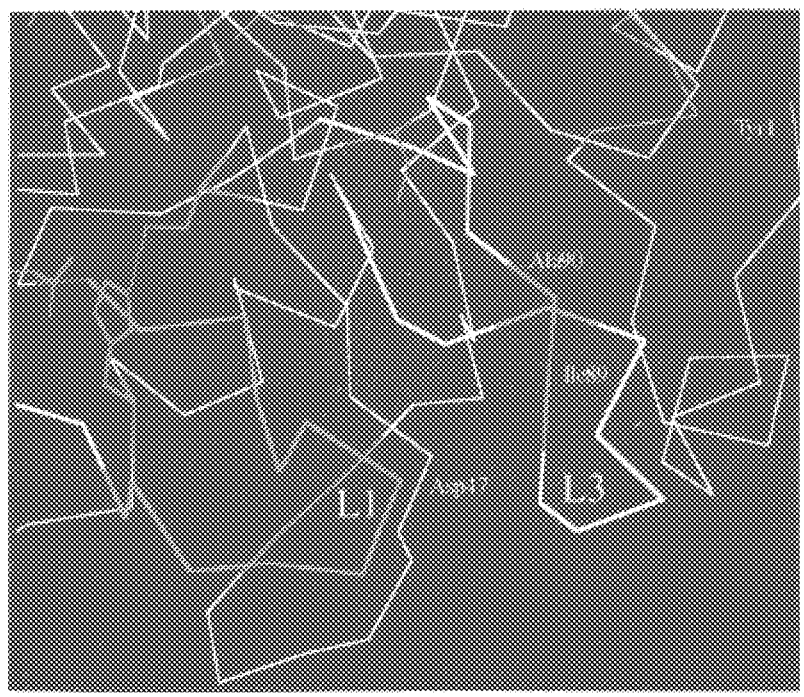
Figure 5B:
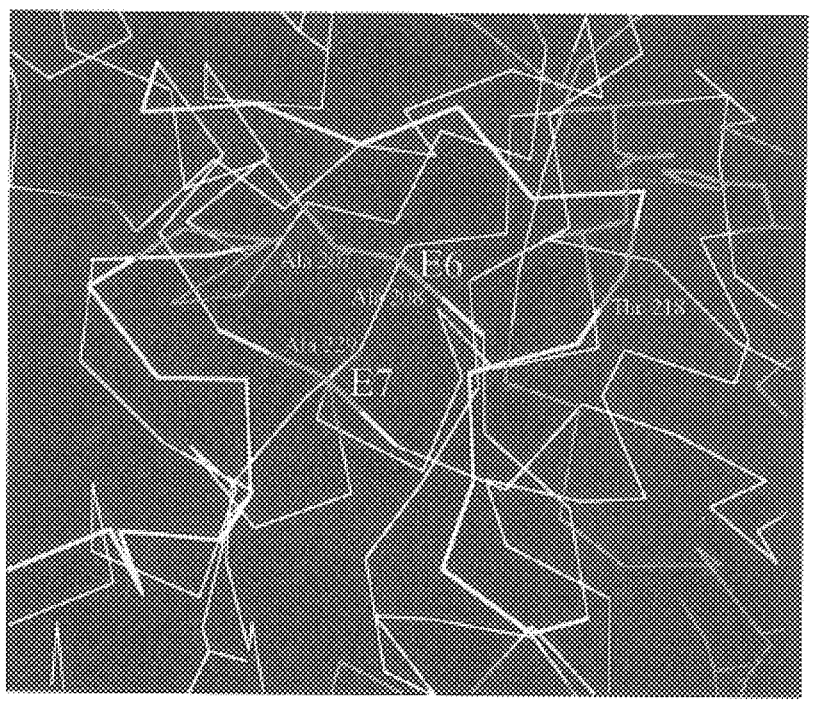
Figure 5C:
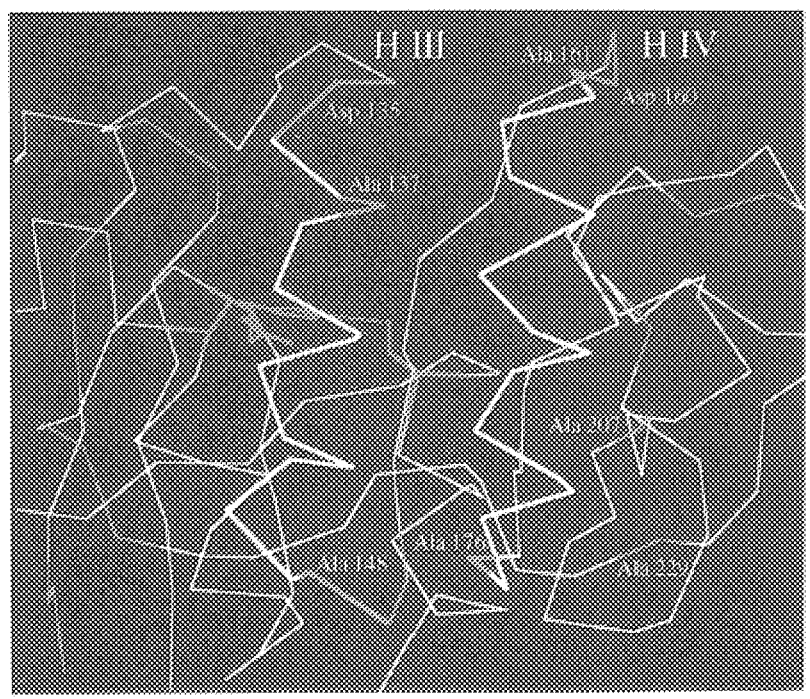

FIGS. 5A, 5B and 5C are pictorial representations of three-dimensional models of aerolysin. The models were built using the Biosyn Homology program with the tertiary structure of the thermitase as a starting point. Residue numbering follows equivalent sites in the *P. aerophilum* sequence. Numbering of secondary structure elements is from FIGS. 6 and 7. FIG. 5A shows clustering of thermophilic residues from two surface loops L1 and L3; FIG. 5B shows thermophilic sites in two adjacent extended strands E6 and E7 linked by loop L8; and FIG. 5C shows thermophilic sites on each side of surfaces helices III and IV.

Figure 6B:
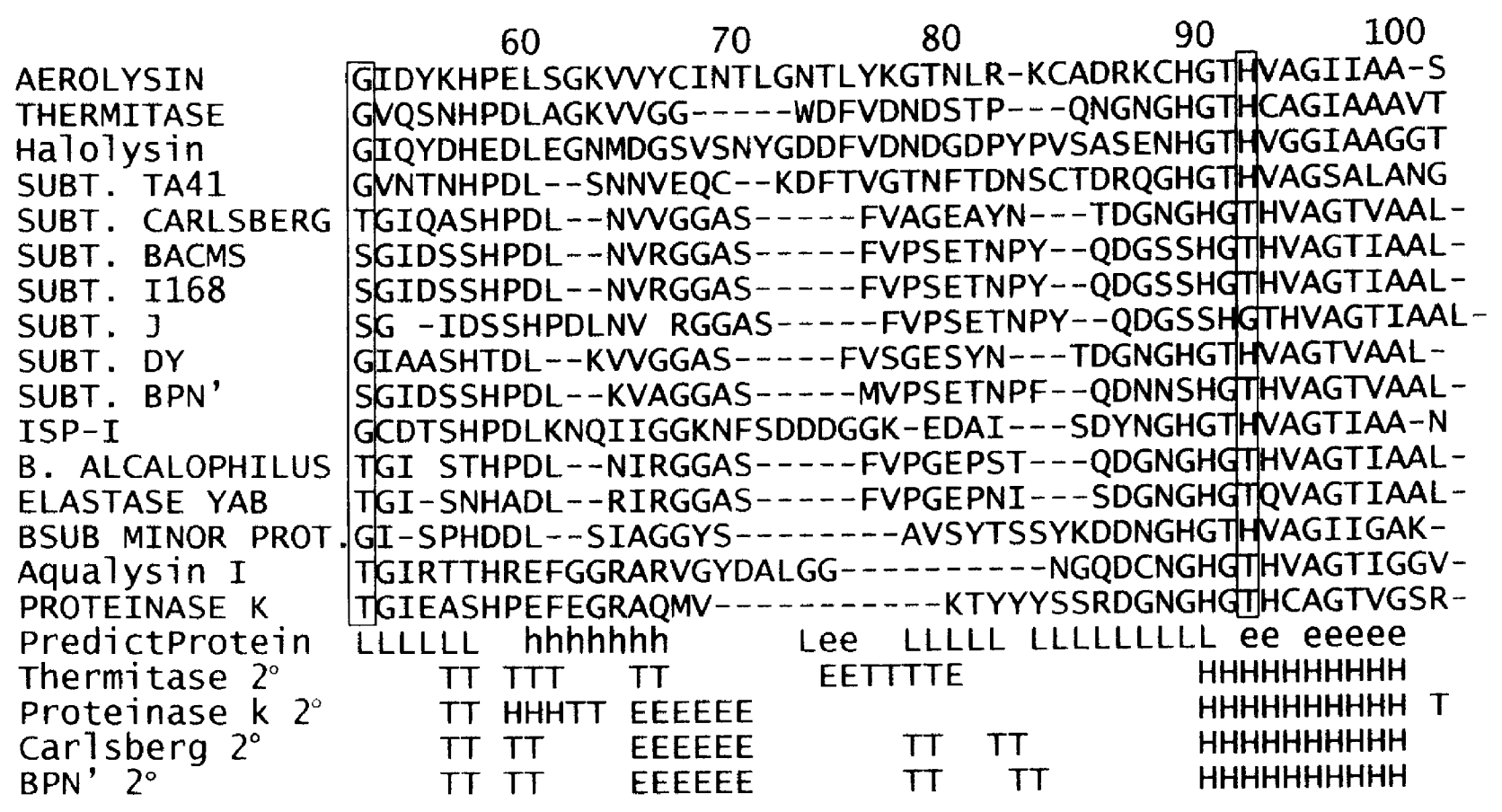

FIGS. 6 and 7 show a comparison of the amino acid sequence of aerolysin to other subtilisins with similar properties.

DETAILED DESCRIPTION OF THE INVENTION

The present invention involves the discovery of a new serine protease which exhibits proteolytic activity at temperatures ranging from 75° C. to 130° C. This new protease is a subtilisin which has been given the name "aerolysin". The amino acid sequence for aerolysin is set forth in sequence ID No. 3.

Aerolysin was initially isolated from the rod-shaped hyperthermophilic archaeum *Pyrobaculum aerophilum. P. aerophilum* was first isolated from a boiling marine water hole at Maronti Beach, Ischia, Italy. The isolation and characterization of *P. aerophilum* is set forth by Völkl et al. (3). *P. aerophilum* grows optimally at 100° C. and pH 7.0. Analysis of the supernatant of a batch culture of *P. aerophilum* reveals that about two thirds of the aerolysin present in the cell is located in the cell envelope fraction with the other third being found in the cytoplasm fraction. No activity is present in the supernatant.

Cloning and Sequencing of Aerolysin

Randomly chosen clones from 1–2 kb genomic DNA library and a poly A primed cDNA library of *P. aerophilum* were sequenced according to conventional procedures. One of the genomic clones (GSPA-35) carried a 1 kb insert with an open reading frame matching the N-terminal sequence of various *Bacillus sp.* subtilisins.

To clone the remainder of the gene, chromosomal DNA of *P. aerophilum* was digested with restriction endonucleases and probed by a Southern blot hybridization with a radiolabeled 18-mer oligonucleotide derived from GSPA-35. Fragments hybridizing to the probe were recovered and subcloned (FIG. 1). Additional plaque lift hybridizations recovered several clones from the poly A cDNA library containing the subtilisin gene. The complete sequence is given in FIG. 1 and sequence ID No. 1. Comparison of the cDNA and genomic sequences showed no introns were present, despite a report of an intervening sequence in *P. aerophilum* 16S rRNA (13). Some cDNA clones started well upstream of the predicted amino terminus. This, and the fact that primer extension experiments gave signals 74 and 400 bases upstream of the ORF indicates that transcription may proceed from an upstream promoter. Sequencing of other cDNAs from *Pyrobaculum aerophilum* has shown that many transcripts are polycistronic.

The translated amino acid sequence (FIG. 1 and sequence ID No. 2) shows a long open reading frame starting 83 amino acids upstream of sequence homology to various subtilisins. The first 15 amino acids encoded by this region showed similarities to leader sequences from subtilisins Carlsberg, BPN', 1168 and *T. aquaticus* aqualysin I. The intervening region is not homologous to any known protein and appears to be the N-terminal peptide autocatalytically cleaved on subtilisin's export from the cell (Terada et al. 1990). The amino acid sequence of the proteolytically active enzyme remaining after cleavage is set forth in sequence ID No. 3. Based on these considerations, methionine was assigned as the initiator for the protein, as well as a potential cleavage site for the mature protein. The end of the gene is clearly defined by 5 stop codons. The first stop codon appeared 15 bases upstream, comparable in position to the end of the gene in several Bacillus species, and was followed by a poly T region.

The materials and methods used to conduct the cloning and sequencing of the aerolysin gene are as follows:

Strains and Media

*P. aerophilum* was grown aerobically in BS-medium at 97° C. as described previously (3). Cells were harvested in the late exponential growth phase by centrifugation and the cell masses were stored at −80° C. until use. *E. coli* strain XL1-Blue is described by the manufacturer (Stratagene, La Jolla, Calif.) as recA1, endA1, gyrA96, thi-1, supE44, relA1, 1ac, [F'proAB 1acl$^q$ZΔM15, Tn10(tet$^r$)]. *E. coli* strain SURE (Stratagene, La Jolla, Calif.) is mcrA, Δ(mcrBC-hsdRMS-mrr)171, supE44, thi-1, 1-, gyrA96, relA, lac, recB, recJ, sbcC, umuC::Tn5 (kan$^r$), uvrC, [F'proAB 1acl$^q$ZDM15, Tn10(ter$^r$)].

Luria Broth (LB) media for growing the *E. coil* strains were prepared as described by Miller (27). LB was supplemented with 0.2% maltose and 10 mM magnesium sulfate when strains were grown before and during 1 phage infection. NYC broth contained per liter of distilled water 5 g NaCl, 2 g $MgSO_4$×7 $H_2O$, 5 g Yeast Estract (Difco), and 10 g NZ Amine (casein hydrolysate; Sigma). The pH was adjusted to 7.5 with NaOH. Agar plates contained 1.5% agar (Difco) and top agarose contained 0.7% agarose (Bio-Rad) instead of agar. SM buffer contained 5.8 g NaCl, 2.0 g $MgSO_4$×7 $H_2O$, 50 ml 1 m Tris/HCl, pH 7.5, and 5 ml 2% gelatin per liter of water. Ampicillin was added to 100 μg/ml and tetracycline to 20 μg/ml medium as described by Miller (27). Tetracycline was not added to media supplemented with maltose and magnesium sulfate.

DNA Isolation and Characterization

DNA from selected λ clones was isolated according to Sambrook et al. (29). Plasmid DNA was isolated by the alkaline lysis procedure as described by Kraft et al. (30). Prior to sequencing, the DNA was analyzed by restriction mapping and agarose gel analysis as described by Sambrook et al. (29).

Plaque lift, colony lift, and Southern hybridizations of agarose gels were carried out according to Sambrook et al. (29) using membranes from Bio-Rad. For the hybridizations, 18-mer oligonucleotide probes, radio-labeled with $\gamma^{32}$P-dATP were used. Hybridization was performed by shaking overnight at 50° C. The membranes were washed in 20 mM $Na_2HPO_4$, 5% SDS at 50° C. for 45 minutes covered with Saran Wrap®, and exposed to Kodak® XAR film.

Sequencing and Data Analysis

Clones from the oligo-dT primed library and genomic libraries were sequenced by the Sanger chain termination method using Sequenase Version 2.0 kit (US Biochemical) and α$^{32}$P-dATP (NEN). Sequencing products were separated on 6% polyacrylamide-urea gels at two intervals to obtain overlapping sequencing runs.

A schematic diagram of the aerolysin gene is set forth in FIG. 4

Three Dimensional Structure of Aerolysin

Three-dimensional models of the aerolysin were established using the Insight II and Homology programs from Biosyn Technologies (San Diego, Calif.). The structurally conserved regions of thermitase were used for creating the model, but refinement of the loop structures was not attempted. In a previous study comparing predicted and actual structures for thermitase, it was found that molecular dynamics and energy minimization were inadequate to select the correct loop conformation for subtilisins (31).

The three-dimensional models of aerolysin are set forth in FIGS. 5A, 5B and 5C. FIG. 5A shows clustering of thermophilic residues from two surface loops L1 and L3; FIG. 5B shows thermophilic sites in two adjacent extended strands E6 and E7 linked by loop L8; and FIG. 5C shows thermophilic sites on each side of surfaces helices III and IV.

A number of subtilisins having similar sequences were identified by BLAST searches (28). The programs CLUSTALV (14) and PredictProtein (15) were used. The PredictProtein server generated a multiple sequence alignment and a secondary structure prediction for the *P. aerophilum* protein. The results are shown in FIGS. 6 and 7. To make the figures, the sequences were aligned with the PredictProtein output and known secondary structures of thermitase, Carlsberg, BPN', and proteinase K.

In FIGS. 6 and 7, the amino acid sequence of aerolysin is aligned with 14 subtilisins and subtilisin-like serine proteases. The first 16 lines of the comparison show the alignment generated using the CLUSTALV algorithm. The bottom of the figure shows the secondary structure prediction from the PredictProtein algorithm, along with known secondary structures for several of the subtilisins in the alignment. Secondary structures are numbered with H=helix, E=extended, and L=loop/turn. Active site residues are boxed. Uppercase letters are "strong" (85% cutoff) predictions, lowercase are "weak" (75% cutoff) predictions according to the PredictProtein algorithm. Residues in bold represent the carboxyl portion of the "prepro" peptide cleaved from the mature protein, when known. Numbering of sequences used in this specification proceeds from the first residue of the mature peptide when known. This residue is indicated in the alignment by double underlining. Otherwise, the first residue listed in the alignment is used for numbering. A "* * * *" at the sequence end indicates that a carboxy-terminal portion of the protein is not included in the alignment.

Pairwise similarity scores (percentile) are listed at the end of each sequence. AEROLYSIN=protease from *Pyrobaculum aerophilum*. THERMITASE=Thermitase from *Thermoactinomyces vulgaris* (16). Halolysin=Halolysin from an unnamed halophylic archaebacteria (18). SUBT. TA41= subtilisin from antarctic *B. subtilis* strain TA41 (20). SUBT. CARLSBERG=Subtilisin Carlsberg (Betzel et al. 1993). SUBT. BACMS=Subtilisin Bacins (21). SUBT. 1168= subtilisin 1168 (22). SUBT. J=Subtilisin J (Jang et al. 1992). SUBT. DY=Subtilisin DY (Betzel et al. 1993). SUBT. BPN'=Subtilisin BPN'(4). ISP.1=ISP.1 (23). SUBT. PB92= Subtilisin from *Bacillus alcalophilus* (24). ELASTASE YAB=Elastase YaB (Kancko et al. 1989). BSUB MINOR PROT.=minor protease from *B. subtilis*. (25). PROTEINASE K=proteinase K from *Tritirachium album* (26). Aqualysin I=Aqualysin I from *Thermus aquaticus* (17). PredictProtein=Secondary structure prediction of PredictProtein algorithm for aerolysin, Thermitase 2°, Carlsberg 2°, BPN 2°=secondary structures of Thermitase proteinase K, and subtilisin Carlsberg, and subtilisin BPN', respectively.

The alignment similarity scores identified the *P. aerophilum* sequence as most similar to Gram-positive subtilisins, but PredictProtein identified thermitase from *Thermoactinomyces vulgaris* (16) as having the most similar structure. Similarity to other serine proteases was much weaker. In particular, the *P. aerophilum* sequence showed weak homology to aqualysin I. produced by *Thermus aquaticus* (17), and halolysin, a serine protease from a moderately thermophilic (60° C.) and halophilic archaeum (18). Neutral proteases such as thermolysin (19), despite their structural similarity, were not recovered by BLAST or PredictProtein, and were not included in the alignment.

The above multiple sequence alignment of aerolysin with 14 different serine type proteases shows that subtilisins from Gram-positive bacteria, rather than archaeal or eukaryal serine proteases, have the greatest homology. In view of the above demonstrated relationship of aerolysin to subtilisins, aerolysin will be useful in the same type of applications in which these other subtilisins and serine proteases are presently being used.

Aerolysin may be used in the same manner as is conventionally known for previous subtilisins. A major present use for aerolysin is as an additive in detergent compositions to enhance removal of protein stains. The amount of aerolysin used as a detergent additive is approximately the same amount as is used for other subtilisins additives. The detergents with which the aerolysin is combined is also the same as those detergents which are presently being used in combination with other subtilisins. Exemplary detergents include laundry detergents and dish soaps. Subtilisins are commonly used in many detergents and aerolysin is used in the same manner. An advantage of aerolysin is that it remains stable in aqueous solutions with detergents at temperatures on the order of 75° C. to about 130° C. Accordingly, it provides effective proteolytic break down of protein stains during high temperature laundering operations. Other exemplary uses for aerolysin include use as a hair removal agent in the tanning industry.

One way to obtain small amounts of aerolysin is to cultivate *P. aerophilum*, form a cell homogenate and isolate the enzyme from the resulting cell paste. Viable colonies of *P. aerophilum* may be found at Maronti Beach and viable cultures are also maintained at the Department of Microbiology and Molecular Genetics at the University of California at Los Angeles (UCLA). Cultures of *P. aerophilum* are also publicly available at DSM located in Braunsweig, Germany.

An exemplary procedure for cultivating *P. aerophilum* is as follows:

An isolate of *P. aerophilum* was cultivated in BS medium, containing the following (per liter of double-distilled $H_2O$: $NaHCO_3$, 2.2 g; $NH_4Cl$, 0.25 g; $KH_2PO_4$, 0.07 g; $(NH_4)_2Fe(SO_4)_2.6H_2O$, 2 mg; $(NH_4)_2Ni(SO_4)_2.2H_2O$, $_2$ mg; $NaSeO_4$, 0.1 mg; $Na_2WO_4.2H_2O$, 0.1 mg; trace mineral solution (1), 10 ml; marine medium ($KNO_3$ omitted [39]), 125 ml; synthetic sea water (17), 125 ml. For determination of salt dependence of growth, the salt concentration in the medium was adjusted with NaCl; pH was adjusted to 7.0 with $H_2SO_4$. BSY medium contained 0.05% yeast extract (Bacto; Difco, Detroit, Mich.) in addition. The final concentration of other substrates used was 0.05% (wt/vol). The $KNO_3$ and $KNO_2$ concentrations were 0.1 and 0.01% (wt/vol), respectively. Strictly anaerobic culture medium was obtained according to the anaerobic technique of Balch and Wolfe (8). Oxygen was reduced by adding 0.05% $Na_2S.9H_2O$ with resazurin (5 µg/l) as the redox indicator. Microaerobic medium was prepared as described previously (9). Prior to autoclaving, the medium was dispensed in 10-ml aliquots into 120-ml serum bottles which were stoppered, and the gas phase was exchanged with the desired gas mixture. As gas phases, $H_2$—$CO_2$ or $N_2$—$CO_2$ (300 kPa; 80:20, vol/vol) was used routinely. For aerobic cultivation with organic and inorganic substrates, 1 or 0.6% $O_2$ (by volume) was added to these gas phases.

Metabolic studies and analyses of end products were performed in a 1-liter glass fermentor containing 700 ml of medium. The fermentor was operated at 97° C. and stirred with 150 rpm without overpressure. For aerobic growth conditions, it was aerated with filter-sterilized air (20 ml/minute). For anaerobic growth, the medium was gassed with approximately 30 ml of $N_2$—$CO_2$ (80:20, vol/vol) per minute.

For plating, BSY medium was solidified with 0.6% Gelrite (Kelco, San Diego, Calif.). The plates were incubated in a pressure cylinder (1) under $N_2$—$CO_2$ (80:20; 200 kPa) for anaerobic growth and under approximately 100 kPa of air (atmospheric pressure) plus 100 kPa of $N_2$—$CO_2$ (80:20) for aerobic growth.

Cell masses were grown anaerobically at 100° C. under stirring (150 rpm) in a 300-liter enamel-protected fermentor (HTE Bioengineering, Wald, Switzerland) pressurized with 100 kPa of $N_2$—$CO_2$ (80:20, vol/vol) and continuous gassing (2.5 liters of $N_2$—$CO_2$ per minute). Packed cell masses exhibited a dark-green color. Under aerobic growth conditions, the fermentor was operated at 97° C. without overpressure by aerating (2.5 liters of air per minute) and stirring (150 rpm). Cell masses showed a light brown color with a touch of green. Cells were harvested in the late exponential growth phase by centrifugation and the cell masses stored at 80° C.

About 1 g of frozen cell paste was resuspended in 10 ml 50 mM Tris/HCl pH 8.0 supplemented with 1 mM $CaCl_2$ and the cells mechanically opened by vortexing in the presence of glass pads. The cell homogenate was separated into cytoplasmic and cell envelope fraction by centrifugation at 15.000×g for 30 minutes in a Beckmann JA-20 rotor. The cell envelope fraction was washed twice in the same buffer used above.

Proteolytic activity of aerolysin was confirmed by the hydrolysis of casein according to the method of Kunitz (10), 100 µl cell envelope fraction (CEF) was added to 0.5 ml of 0.6% casein (Merck) or 0.2% azocasein (Serva) in 50 mM Tris/HCl pH 8.0. After incubation the reaction was stopped by adding 1 ml of 5% trichloroacetic acid and incubating at room temperature for about 30 minutes. The reaction was centrifuged in an eppendorf centrifuge for 10 minutes, and the absorbance of the supernatant at 280 nm when casein and 420 nm when azocasein was used.

Discontinuous SDS-PAGE was performed according to Laemmli (11), except that to the 10% separation gel 0.01% casein (Merck) and 0.1% SDS were added. The 3% stacking gel was supplemented with 0.1% SDS only. Electrophoresis, incubation and fixing of the gel was done as described by Connaris (12) except that the gel was incubated at 95° C. in 50 mM Tris/HCl, 1 mM $CaCl_2$.buffer pH 8.0. The analysis of the supernatant of a batch culture, of the cell envelope fraction, and the cytoplasmic fraction according to the above procedure showed that about two thirds of the proteolytic activity was associated with the cell envelope fraction and about one third was found in the cytoplasm. No activity was present in the supernatant. Below 75° C. no significant proteolytic activity was found. Activity was highest at neutral to alkaline pH and temperatures from 100° C. up to 130° C. Substrate containing denaturing SDS PAGE showed a band at MW 60 kD after incubation for 30 minutes at 95° C. After 60–90 minutes of incubation up to four additional bands appeared. The additional bands are believed to be due to self-digestion of the aerolysin.

P. aerophilum is like many other hyperthermophilic organisms in that cultivation in large quantities for commercial use is difficult. The high growth temperatures, low growth titers, strict anaerobiosis, sulfur dependence and other features makes large scale production of cell homogenates undesirable. Accordingly, the preferred method for producing aerolysin is by genetically engineering a more easily cultivated organism so that it expresses the active protease.

Suitable organisms which can be genetically engineered to express aerolysin include mesophiles such as *E. coli* and other organisms such as *B. subtilis.*

The expression of aerolysin can be accomplished in the same manner as the expression of other subtilisins. It has been demonstrated that when aqualysin I from *Thermus aquaticua* is expressed in *E. coli*, its N-terminal peptide is correctly removed and the precursor protein is exported to the periplasmic space (Terada et al., 1990). Subsequent heat treatment at 65° C. causes autocatalytic cleavage of the N-terminal peptide which activates the protease.

Recent studies (Frömmel and Sander, 1989; Menendez-Arias and Argos, 1989) have shown a pattern of substitutions associated with protein stability at high temperatures. In a preliminary analysis of the aerolysin sequence sites potentially contributing to thermostability were scored manually, using the statistically significant exchanges from Table 3 in Menendez-Arias and Argos (7). A site was scored positive if the transition was predicted by the table, and if it was shared by three or fewer of the 15 proteins in the alignment. Transitions were considered strongly thermophilic if the transitions were confined to the moderately thermophilic proteins thermitase, aqualysin I, halolysin, and proteinase K. A summary of the results is found in Table 1.

TABLE 1

| PA[A] | TM[B] | CS[C] | TA41[D] | Transition | Secondary |
|---|---|---|---|---|---|
| Predicted from Transition Tables | | | | | |
| Ala 42 | Ala 27 | Gly 20 | Thr 33 | Hyd. → Ala | turn C-terminal to helix H1 |
| Glu 62 | Asp 47 | Asp 41 | Asp 54 | Asp → Glu | turn in loop L2 |
| Ser 109 | Gly 88 | Gly 79 | Gly 99 | Gly → Ser | loop L4 (adj. to Glu 62) |
| Ala 110 | Ile 89 | Val 80 | Val 100 | Hyd. → Ala | loop L4 (adj. to Glu 62) |
| Ala 111 | Ala 90 | Leu 81 | Leu 101 | Hyd. → Ala | loop L4 |
| Ala 137 | Ala 116 | Val 107 | Ala 127 | Hyd. → Ala | N-terminal helix H3 |
| Ala 148 | Ala 127 | Met 118 | Thr 138 | Hyd. → Ala | C-terminal to helix H3 |
| Ala 161 | Asn 140 | Ser 131 | Ser 156 | Asn/Ser → Ala | loop terminal to helix H4 |
| Ala 176 | Ser 155 | Val 146 | Val 171 | Hyd. → Ala | Turn C-terminal to helix H4 |
| Ala 207 | Val 181 | Val 176 | Leu 202 | Hyd. → Ala | extend. E6 (adj. to Ala 229) |
| Ala 208 | Ala 182 | Gly 177 | Glu 203 | Gly → Ala | extend. E6 (adj. to Ala 229) |
| Thr 218 | Ser 192 | Ser 187 | Val 213 | Ser → Thr | turn in loop L8 |
| Ala 229 | Ala 203 | Met 198 | Thr 224 | Hyd. → Ala | extend. E7 (adj. to Ala 181, 182) |
| Ser 248 | Ser 220 | Asn 217 | Ser 257 | Asn~Gly → | extended E8 |

TABLE 1-continued

| PA[A] | TM[B] | CS[C] | TA41[D] | Transition | Secondary |
|---|---|---|---|---|---|
| | | | | Ser~Gly | |
| Ala 308 | Ala 273 | Val 269 | Ala 311 | Hyd. → Ala | N-terminal helix H7 |
| Counterpredictions | | | | | |
| | | | | | |
| Thr 258 | Ala 232 | Ala 227 | Ala 260 | Ala → Thr | buried helix H5 |
| Val 260 | Val 234 | Ala 229 | Ala 262 | Ala → Val | buried helix H5 |
| Addition of negative charge at N-terminal of alpha helices | | | | | |
| | | | | | |
| Asp 135 | Thr 113 | Gly 105 | Asp 125 | unch. → (+) | N-terminal helix H3 |
| Asp 160 | Gly 139 | Gly 130 | Glu 155 | unch. → (+) | N-terminal helix H4 |
| Asp 279 | Ser 246 | Ser 243 | Val 283 | unch. → (+) | N-terminal helix H6 |
| Glu 280 | Asn 247 | Gln 244 | Asp 284 | unch. → (+) | N-terminal helix H6 |
| Asp 307 | Asn 272 | Asn 268 | Ile 310 | unch. → (+) | N-terminal helix H7 |
| Counterpredictions | | | | | |
| | | | | | |
| Arg 90 | Gly 68 | Gly 60 | Arg 79 | unch. → (+) | N-terminal Helix H2 |
| Lys 91 | Asn 69 | Asn 61 | Asn 80 | unch. → (+) | N-terminal Helix H2 |

[A]PA denotes *P. aerophilium*,
[B]TM denotes thermitase from *T. vulgaris*,
[C]CS denotes subtilisin Carlsberg and
[D]TA41 denotes Antartic Bacillus strain TA41.

The most common transition replaced a variety of amino acid types with alanine. This result fits several instances in their transition table, but runs counter to their finding that substitutions of increasing hydrophobicity are also stabilizing. In *P. aerophilum* sequence, transitions to alanine were observed at least 9 sites, with the only strong counterexamples found at Thr 258 and Val 260. By contrast the Gly→Ala transition, reported as being statistically most frequent by Argos et al. (32) was found at only a single site in the protein. Suggestive evidence for less statistically significant transitions Ser→Thr, Lys→Arg, and Asp→Glu were also found, though several counterexamples examples exist for these cases.

A second class of sites was also noted, in which the *P. aerophilum* subtilisin replaced an uncharged amino acid with aspartic acid. The only subtilisins sharing these transitions were halolysin and TA41 from an Antarctic Bacillus species.

Model Building

Figure 3:
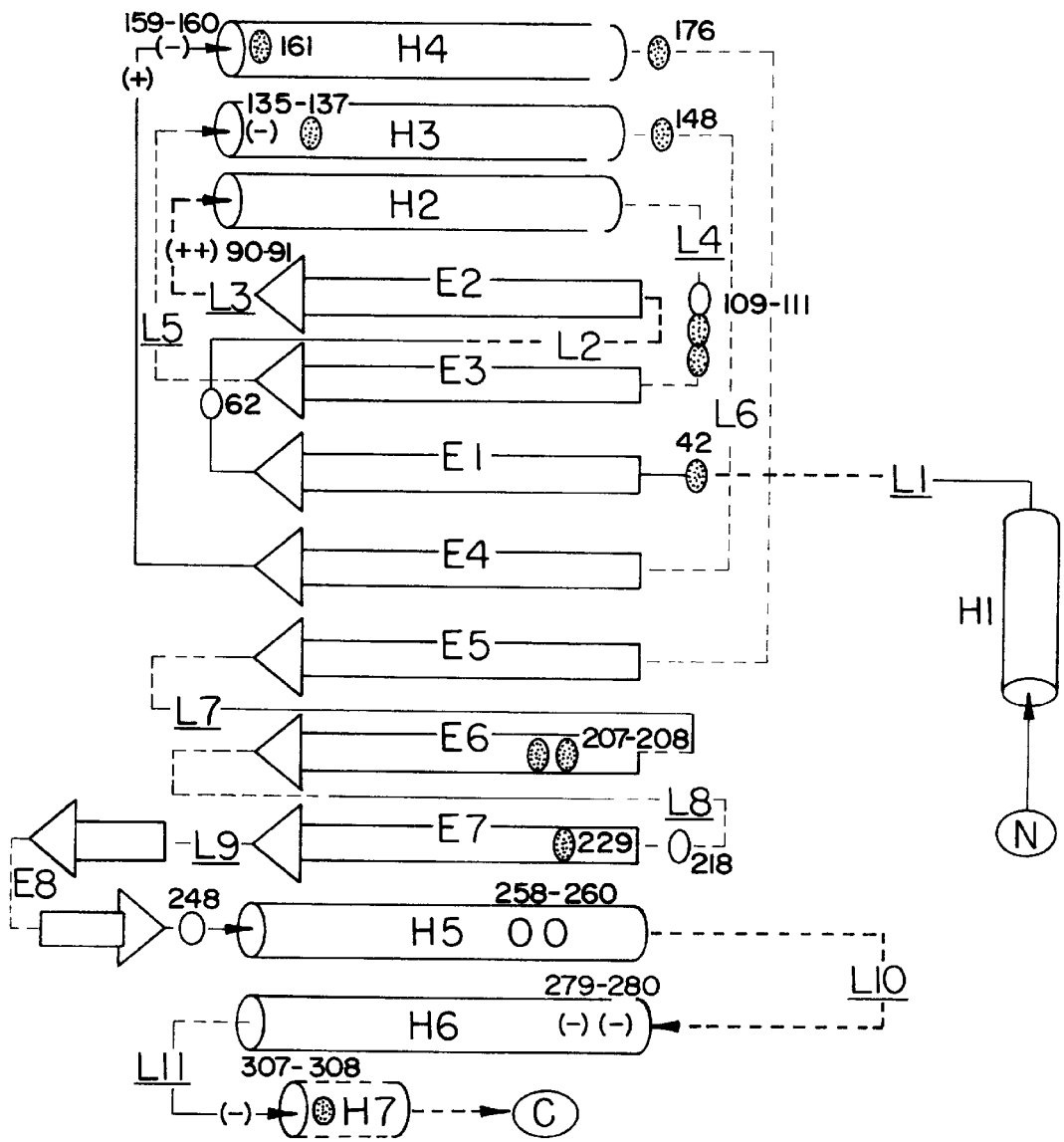
FIG. 3 is a structural cartoon of aerolysin which shows the position of sites potentially involved in thermostability. The cartoon is drawn after Chen and Arnold (2), variable regions are from Siezen (1). Numbering and secondary structure designation is after the aerolysin sequence in FIGS. 1 and 2. Heavy dashed lines indicate loop regions that are larger in the aerolysin sequence, compared to Gram-positive subtilisins. Black circles indicate positions of thermostable transitions in which a bulky hydrophobic amino acid is replaced by alanine. Plus (+) and minus (−) signs indicate positions where the charge addition or replacement might affect the stability of an alpha-helix. Partly shaded circles indicate other transitions expected to have smaller effects on thermostability after Menendez-Arias and Argos (7). Clear circles indicate sites where the sequence transition is the reverse of that predicted by Menendez-Arias and Argos (7).

In order to further examine the structure of the transition sites in *P. aerophilum* aerolysin, two models were generated. The first, shown in FIG. 3, maps data from Table 1 onto a cartoon of secondary structure drawn after Chen and Arnold (2). The sequence/secondary structure alignments in FIG. 3 were used to assign sites to the structure. Five of the alanine transitions map to the amino and carboxyl ends of helices H3, H4, and H7. Since these helices are on the protein surface, alanine replacement may result in more stable packing against the hydrophobic core and/or decreased helical flexibility. The counterexamples at positions 258–260 (where the *P. aerophilum* sequence has a bulky hydrophobic amino acid relative to other subtilisins) map to internal hydrophobic helix H5. Since this helix is buried, requirements for its stability may differ from surface helices.

The transitions to aspartic acid also show correlation with secondary structure, mapping to the N-terminal ends of helices H3, H4, H6, and H7 (FIG. 5C). Aspartic acid is common at the N-terminus of alpha-helices, where it can interact with the helix dipole to increase stability (Sali et al. 1988). However, the Antarctic subtilisin TA41 has even more negative charges than aerolysin in these positions, which raises doubts as to their role in thermostability.

The remaining sites map to variable surface loops and beta strands E6 and E7. In order to interpret these sites, a simple three-dimensional model was generated using the sequence alignment and Biosym's Homology program. Examination of the tertiary structure model reveals that several of the remaining sites may be in physical contact with each other (FIGS. 5A and 5B). In thermitase, the turn containing Asp 47 passes near the loop containing Gly 88 and Ile 89. The corresponding residues in the *P. aerophilum* sequence all show thermophilic transitions, being at Glu 62, Ser 109, and Ala 110, respectively. Though the true structure of the loop regions cannot be determined from the model, the clustering of thermostable sites may indicate that the loops L4 and L6 continue to interact in *P. aerophilum* subtilisin. A similar spatial clustering is found for residues Ala 207, Ala 208, and Ala 229 (thermitase residues Val 181, Ala 182, and Ala 203). These residues are in the adjacent extended strands E6 and E7, connected by loop L8.

The present invention covers not only the specific aerolysin protease set forth in Seq. ID Nos. 2 and 3, but also covers modified aerolysin proteases wherein one or more amino acid substitutions have been made. For the purposes of this specification, thermally stable modified sequences of aerolysin are those proteases which have at least 90 percent homology with aerolysin and maintain at least 90 percent of the high temperature proteolytic activity demonstrated by aerolysin on a standard protein such as casein. Such thermally stable modified sequences of aerolysin can be easily prepared and identified by those skilled in the art. Procedures for substituting amino acids into a wide variety of subtilisins are well known and are widely practiced in conventional procedures for engineering other subtilisins. Once a substitution has been made to produce modified protease having at least 90 percent homology with aerolysin, it is then a simple matter to experimentally verify that the modified protease meets the proteolytic requirements of the present invention (i.e. 90 percent of the proteolytic activity of aerolysin at temperatures of between about 75° C. and 130° C.).

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

BIBLIOGRAPHY

1. Siezen, R. J., de Vos, W. M., Leunissen, J. A. and Dijakstra, B. W., Homology Modelling and Protein Engineering Strategy of Subtilases, the Family of Subtilisin-Like Serine Proteinases, *Protein Engineering*, Vol. 4, no. 7, pp. 719–737 (1991).
2. Chen, K. and Arnold, F. H. (1993) Tuning the activity of an enzyme for unusual environments: sequential random mutagenesis of subtilisin E for catalysis in dimethylformamide. *Proc. Natl. Acad. Sci. USA* 90(12), 5618–22.
3. Volkl, et al., Applied and Environmental Microbiology, September 1993, p. 2918–2926.
4. Pantoliano, M. W., Whitlow, M., Wood, J. F., Dodd, S. W., Hardman, K. D., Rollence, M. L. and Bryan, P. N. (1989) Large increases in general stability for subtilisin BPN' through incremental changes in the free energy of unfolding. *Biochemistry* 28, 7205–7213.
5. Narhi, L. O., Stabinsky, Y., Levitt, M., Miller, L., Sachdev, R., Finley, S., Park, S., Kolvenbach, C., Arakawa, T. and Zukowski, M. (1991) Enhanced stability of subtilisin by three point mutations. *Biotechnol. App. Biochem.* 12, 12–24.
6. Eijsink, Vincent G., H. Gerrit Vriend, Bertus van den Burg, J. Rob van der Zee, and Gerard Venema (1992)

Increasing the thermostability of a neutral protease by replacing positively charged amino acids in the N-terminal turn of alpha-helices. *Protein Engineering* 5:165–170.
7. Menendez-Arias L. and Argos P. (1989) Engineering protein thermal stability. Sequence statistics point to residue substitutions in alphahelices. *J. Mol. Biol.* 206, 397–406.
8. Balch, W. E. and R. S. Wolfe (1976) New approach to the cultivation of methanogenic bacteria: 2-mercaptoethanesulfonic acid (HS-CoM)-dependent growth of *Methanobacterium reminantium* in a pressurized atmosphere. *Appl. Environ. Microbiol.* 32:781–791.
9. Huber, R. T., Wilharm, D., Huber, A. Trincone, S., Burggraf, H., König, R., Rachel I. Rockinger, H. Fricke and K. O. Stetter (1992) *Aquifex pyrophilus* gen. nov. sp. nov., represents a novel group of marine hyperthermophilic hydrogen-oxidizing bacteria. *Syst. Appl. Microbiol.* 15:340–351.
10. Kunitz, M. (1947) Crystalline soybean trypsin inhibitor II. General properties. *J. Gen. Physiol.* 30, 291–310.
11. Lammli, U. K. (1970) Cleavage of structural proteins during the assembly of the head of bacteriophage T4. *Nature* (London) 227, 680–685.
12. Connaris, H., D. A. Cowan and R. J. Sharp (1991) Heterogeneity of proteinases from the hyperthermophilic archaeobacterium *Pyrococcus furiosus*. *J. Gen. Microbiol.* 137, 1193–1199.
13. Burggraf, S., Larsen, N., Woese, C. R. and Stetter, K. O. (1993) An intron within the 16s ribosomal RNA gene of the archaeum *Pyrobaculum aerophilum*. *Proc. Natl. Acad. Sci. USA* 90, 2547–2550.
14. Higgins, D. G. and Sharp, P. A. (1989) Fast and sensitive multiple sequence alignments on a microcomputer. *CABIOS* 5, 151–153.
15. Rost, B., Sander C. (1993) submitted to *J. Neural Systems*.
16. Meloun, B., Baudys, M., Kostka, V., Hausdorf, G., Frömmel, C., and Höhne, W. E. (1985) Complete primary structure of thermitase from *Thermoactinomyces vulgaris*, and its structural features related to the subtilisin-type proteinases. *FEBS Lett.* 183, 195–200.
17. Terada, I., Kwon, S. T., Miyata, Y., Matsuzawa, H. and Ohata, T. (1990) Unique precursor structure of an extracellular protease. Aqualysin I, with NH2 and COOH-terminal Pro-sequences and its processing in *Escherichia coli*. *J. Biol. Chem.* 265(12), 6576–6581.
18. Kamekura, M., Seno, Y., Holmes, M. L. and Dyall-Smith, M. L. (1992) Molecular cloning and sequencing of the gene for a halophilic alkaline serine protease (Halolysin) from an unidentified halophilic Archaea strain (172PI), and expression of the gene in *Haloferax volcanii*. *J. Bacteriol.* 174(3), pp.736–742.
19. Paupitt, R., Karlsson, R., Picto, D., Jenkins Ann-Solfie Niklaus-Reimer, J., and Jansonius, K. (1988) Crystal structure of neutral protease from *Bacillus cereus* refined at 3.0 Å resolution and comparison with the homologous but more thermostable enzyme thermolysin. *J. Mol. Bio.* 199, 525–537.
20. Davail, S., Feller, G., Narinx, E., and Gerday, C. (1992) Sequence of the subtilisin-encoding gene from an Antarctic psychrotroph Bacillus TA41. *Gene* 119(1): 143–144.
21. Svendsen, I., Genov, N., Idakieva, K. (1986) Complete amino acid sequence of alkaline mesenteric peptidase: a subtilisin isolated from a strain of *Bacillus mesentericus*. *FEBS LETT.* 196, 228–232.
22. Stahl, M. L., Ferrari, E. (1984) Replacement of the *Bacillus subtilis* subtilisin structural gene with an in vitro derived deletion mutation. *J. Bacteriol.* 158, 411–418.
23. Rufo, G. A. Jr., Sullivan, B. J., Sloma, A., Pero, J. (1990) Isolation and characterization of a novel extracellular metalloprotease from *Bacillus subtilis*. *J. Bacteriol.* 172 (2), 1019–23.
24. van der Laan, J. M., Teplyakov, A. V., Kelders, H., Kalk, K. H., Misset, O., Mulleners, L. J., Dijkstra, B. W. 1992) Crystal structure of the high-alkaline serine protease PB92 from *Bacillus alcalophilus*. *Protein Engineering* 5(5), 405–11.
25. Sloma, A., Rufo, G. A., Jr., Theriault, K. A., Dwyer, M., Wilson, S. W., Pero, J. (1991) Cloning and characterization of the gene for an additional extracellular serine protease of *Bacillus subtilis*. *J. Bacteriol.* 173(21), 6889–95.
26. Gunkel, F. A., Gassen, H. G. (1989) Proteinase K from Tritirachium album Limber. Characterization of the chromosomal gene expression of the cDNA in *Escherichia coli*. *Eur. J. Biochem.* 179(1), 185–94.
27. Miller, J. H. (1992) in *A short course in bacterial Genetics*, Cold Spring Harbor Press, New York, pp. 17–43.
28. Altschul, S. F., Gish, W., Miller, W., Myers, E. W. and Lipman, D. J. (1990) Basic local alignment search tool. *J. Mol. Biol.* 215, 403–410.
29. Sambrook, J., Fritsch, E. and Maniatis, T. (1989) in *Molecular Cloning: A Laboratory Manual*, Cold Spring Harbor Laboratory Press, USA.
30. Kraft, R., Tardiff, J., Krauter, K. S. and Lainwand, L. A. (1988) Using mini-prep plasmid DNA for sequencing double-stranded templates with sequenase. *BioTechniques* 6, 544–546.
31. Frömmel, C. and Sander, C. (1989) Thermitase, a thermostable subtilisin: comparison of predicted and experimental structures and the molecular cause of thermostability, *Proteins* 5, 22–37.
32. Argos, P., Rossmann, M. G., Grau, U. M., Zuber, H., Frank, G., Tratschin, J. D. (1979) Thermal stability of proteins, *Biochemistry* 18, 5698–5703.

What is claimed is:

1. An isolated and purified serine protease which exhibits proteolytic activity at temperatures of between about 75° C. and about 130° C., said protease comprising an amino acid sequence as set forth in SEQ ID NO:3 and thermally stable modified sequences thereof.

2. A serine protease according to claim 1 wherein said amino acid sequence comprises the amino acid sequence set forth in SEQ ID NO:3.

3. An isolated and purified serine protease which exhibits proteolytic activity at temperatures of between about 75° and about 130° C. obtained from *Pyrobaculum aerophilum*.

4. An isolated and purified serine protease which exhibits proteolytic activity at temperature of between about 75° C. and about 130° C., said protease comprising an amino acid sequence having at least 90 percent homology to SEQ ID NO:3.

5. An isolated and purified serine protease which exhibits proteolytic activity at temperature of between about 75° C. and about 130° C., said protease comprising an amino acid sequence having at least 90 percent homology to SEQ ID NO:2.

6. A method for digesting a protein, said method comprising the steps of treating said protein at a temperature of between about 75° C. and about 130° C. with a sufficient amount of a serine protease comprising an amino acid sequence as set forth in SEQ ID NO:3, and thermally stable modified sequences thereof, to thereby digest said protein.

7. A method for digesting a protein according to claim 6 wherein said amino acid sequence of said serine protease comprises the amino acid sequence set forth in SEQ ID NO:3.

8. A solution for use in digesting a protein at temperatures of between about 75° C. and 130° C., said solution comprising:

a serine protease comprising an amino acid sequence as set forth in SEQ ID NO:3 and thermally stable modified sequences thereof; and an aqueous substrate for said serine protease.

9. A solution for use in digesting a protein according to claim 8 wherein said amino acid sequence of said serine protease comprises the amino acid sequence set forth in SEQ ID NO:3.

10. A solution for use in digesting a protein according to claim 8 wherein the temperature of said solution is between about 75° C. and about 130° C.

11. A detergent solution for use in cleaning articles at temperatures of between about 75° C. and about 130° C., said solution comprising:

a serine protease comprising an amino acid sequence as set forth in SEQ ID NO:3 and thermally stable modified sequences thereof;

a detergent; and an aqueous substrate for said serine protease and detergent.

12. A detergent solution for use in cleaning articles according to claim 11 wherein said amino acid sequence of said serine protease comprises the amino acid sequence set forth in SEQ ID NO:3.

13. A detergent solution for use in cleaning articles according to claim 11 wherein the temperature of said detergent solution is between about 75° C. and about 130° C.

14. An isolated nucleotide sequence which encodes a serine protease which exhibits proteolytic activity at temperatures of between about 75° C. and about 130° C., said nucleotide sequence comprising the nucleotide sequence set forth in SEQ ID NO:1.

15. A transformed microorganism which expresses a serine protease as defined in claim 1.

16. A transformed microorganism which expresses a serine protease as defined in claim 2.

17. A transformed microorganism according to claim 15 wherein said organism is selected from the group consisting of *E. coli* and *B. subtilis*.

18. A transformed microorganism which expresses a protein having the amino acid sequence set forth in SEQ ID NO:2.

* * * * *

UNITED STATES PATENT AND TRADEMARK OFFICE
CERTIFICATE OF CORRECTION

PATENT NO. : 5,830,740
DATED : November 3, 1998
INVENTOR(S) : Jeffrey Miller, et al.

It is certified that error appears in the above-identified patent and that said Letters Patent are hereby corrected as shown below:

On The Title Page, [53] Title: "$103^{\circ}C$" should read --$130^{\circ}C$--

On The Title Page, [75] Inventors: "Santo Monk" should read --Santa Monika--

On The Title Page, [56] References Cited, OTHER PUBLICATIONS:

"thermostabilityfrom" should read --thermostability from--

On The Title Page, [56] References Cited, OTHER PUBLICATIONS:

"6663-667" should read --6663-6667--

Signed and Sealed this

Twenty-ninth Day of May, 2001

Attest:

NICHOLAS P. GODICI

*Attesting Officer*   *Acting Director of the United States Patent and Trademark Office*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
  ( A ) LENGTH: 1848 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 244..1446

( x i ) SEQUENCE DESCRIPTION: SEQ ID NO:1:

```
GGAACAAAGC   TGAGCTCACG   GTGCGCGCTC   TAGACTAGTG   ATCCATTGGC   GAGTGACTTG        60

TGAATACTCC   AAGCGCTTTA   CTTAATCCAG   TGGGAGGGCA   AGCTGACTAT   TAGACAAGCC       120

CCCCAGTACT   TCAACGAGTT   AGATTTACAA   TTGAGAATCG   GCGCTGAGGT   GATAGAAACT       180

GCGAAAAGCA   TAGGCGTTTC   TAAAAAAGTT   CAAAAAGAG    TTTCCGCTGT   AATAGACGAA       240

TTA   ATG   TCA   TAA   TAT   TTG   AAA   AGA   CGT   AAA   AAA   CTG   GCT   CAA   TGC   CAA       288
      Met   Ser   Gln   Tyr   Leu   Lys   Arg   Arg   Lys   Lys   Leu   Ala   Gln   Cys   Gln
       1                  5                        10                              15

AGG   TTT   GGC   GGC   ACT   AGT   GGC   ATT   TCT   TCA   AGC   CGC   GAG   ATT   GTA   GTG       336
Arg   Phe   Gly   Gly   Thr   Ser   Gly   Ile   Ser   Ser   Ser   Arg   Glu   Ile   Val   Val
                         20                       25                              30

GGC   TAT   GTC   GAT   TCC   CCT   CCC   AGC   GAA   GCT   TTA   AAA   GAG   TTA   AAT   AAA       384
Gly   Tyr   Val   Asp   Ser   Pro   Pro   Ser   Glu   Ala   Leu   Lys   Glu   Leu   Asn   Lys
                   35                             40                              45

ACA   GGC   GAT   ATT   AAA   ATA   ATA   AAA   CAT   TTA   AAA   GAA   ATC   AAA   GCA   ATT       432
Thr   Gly   Asp   Ile   Lys   Ile   Ile   Lys   His   Leu   Lys   Glu   Ile   Lys   Ala   Ile
                   50                             55                              60

GTA   TTA   AAC   ATT   CCC   GAT   AAT   AAA   ACA   GAG   AAA   CTT   AAG   GAA   AAG   TTA       480
Val   Leu   Asn   Ile   Pro   Asp   Asn   Lys   Thr   Glu   Lys   Leu   Lys   Glu   Lys   Leu
             65                             70                             75

AAA   GGA   GTT   AGA   TAT   ATA   GAG   GAA   GAC   GGC   GTT   GCG   TAT   GGG   TTT   GGT       528
Lys   Gly   Val   Arg   Tyr   Ile   Glu   Glu   Asp   Gly   Val   Ala   Tyr   Gly   Phe   Gly
 80                      85                             90                             95

TTT   TCT   AAT   TAT   ACC   GAT   GTA   CAG   TGG   AAT   GTA   AAA   ATG   ATA   AAC   GCC       576
Phe   Ser   Asn   Tyr   Thr   Asp   Val   Gln   Trp   Asn   Val   Lys   Met   Ile   Asn   Ala
                        100                      105                            110

CCG   CGT   CTG   GGA   CGC   CTA   TTT   TCT   CAC   ATT   TGG   CGA   CGC   GCA   TTT   GGC       624
Pro   Arg   Leu   Gly   Arg   Leu   Phe   Ser   His   Ile   Trp   Arg   Arg   Ala   Phe   Gly
                  115                            120                            125

TAT   GGA   GTT   AAA   GTG   GCG   GTG   CTC   GAC   ACA   GGC   ATT   GAC   TAC   AAG   CAC       672
Tyr   Gly   Val   Lys   Val   Ala   Val   Leu   Asp   Thr   Gly   Ile   Asp   Tyr   Lys   His
            130                            135                            140

CCG   GAG   CTA   TCC   GGC   AAG   GTG   GTT   TAT   TGT   ATT   AAC   ACT   CTC   GGC   AAC       720
Pro   Glu   Leu   Ser   Gly   Lys   Val   Val   Tyr   Cys   Ile   Asn   Thr   Leu   Gly   Asn
145                      150                            155

ACT   CTC   TAC   AAG   GGG   ACA   AAT   TTA   AGG   AAG   TGC   GCC   GAC   AGA   AAA   TGC       768
Thr   Leu   Tyr   Lys   Gly   Thr   Asn   Leu   Arg   Lys   Cys   Ala   Asp   Arg   Lys   Cys
160                     165                            170                            175

CAC   GGC   ACG   CAT   GTA   GCT   GGG   ATA   ATA   GCC   GCT   TCG   TTG   AAT   AAC   GTG       816
His   Gly   Thr   His   Val   Ala   Gly   Ile   Ile   Ala   Ala   Ser   Leu   Asn   Asn   Val
                  180                            185                            190

AGC   GCA   GCC   GGC   GTT   GTG   CCT   AAG   GTG   CAG   TTA   ATA   GCA   GTT   AAG   GTC       864
Ser   Ala   Ala   Gly   Val   Val   Pro   Lys   Val   Gln   Leu   Ile   Ala   Val   Lys   Val
                  195                            200                            205

TTA   TAC   GAC   AGC   GGC   TGG   GGG   TAC   TAT   AGC   GAT   ATT   GCC   GAG   GGG   ATA       912
Leu   Tyr   Asp   Ser   Gly   Trp   Gly   Tyr   Tyr   Ser   Asp   Ile   Ala   Glu   Gly   Ile
            210                            215                            220

ATA   GAG   GCA   GTT   AAA   GCA   GGG   GCT   TTA   ATT   CTA   TCA   ATG   TCC   CTA   GGA       960
Ile   Glu   Ala   Val   Lys   Ala   Gly   Ala   Leu   Ile   Leu   Ser   Met   Ser   Leu   Gly
```

```
                                  225                             230                             235
GGC   CCC   ACA   GAC   GCC   TCT   GTG   TTG   AGA   GAC   GCC   TCG   TAT   TGG   GCC   TAT       1008
Gly   Pro   Thr   Asp   Ala   Ser   Val   Leu   Arg   Asp   Ala   Ser   Tyr   Trp   Ala   Tyr
240                           245                             250                             255

CAA   CAA   GGC   GCT   GTT   CAG   ATA   GCC   GCC   GCT   GGT   AAT   TCA   GGC   GAT   GGC       1056
Gln   Gln   Gly   Ala   Val   Gln   Ile   Ala   Ala   Ala   Gly   Asn   Ser   Gly   Asp   Gly
                        260                           265                             270

GAT   CCC   TTG   ACA   AAC   AAC   GTG   GGG   TAT   CCC   GCC   AAG   TAT   AGC   TGT   GTA       1104
Asp   Pro   Leu   Thr   Asn   Asn   Val   Gly   Tyr   Pro   Ala   Lys   Tyr   Ser   Cys   Val
                  275                           280                             285

ATA   GCA   GCG   GCG   GCG   GTA   GAT   CAA   AAC   GGC   TCC   GTC   CCC   ACG   TGG   AGT       1152
Ile   Ala   Ala   Ala   Ala   Val   Asp   Gln   Asn   Gly   Ser   Val   Pro   Thr   Trp   Ser
            290                           295                             300

AGC   GAC   GGG   CCA   GAG   GTG   GAC   ACC   GCG   GCG   CCA   GGG   GTA   AAC   ATA   TTG       1200
Ser   Asp   Gly   Pro   Glu   Val   Asp   Thr   Ala   Ala   Pro   Gly   Val   Asn   Ile   Leu
      305                           310                             315

TCC   ACA   TAT   CCC   GGC   GGC   AGA   TAC   GCG   TAT   ATG   TCC   GGC   ACA   TCT   ATG       1248
Ser   Thr   Tyr   Pro   Gly   Gly   Arg   Tyr   Ala   Tyr   Met   Ser   Gly   Thr   Ser   Met
320                           325                             330                             335

GCG   ACG   CCT   CAC   GTG   ACT   GGC   GTA   GCG   GCC   TTA   ATA   CAA   GCG   TTG   AGA       1296
Ala   Thr   Pro   His   Val   Thr   Gly   Val   Ala   Ala   Leu   Ile   Gln   Ala   Leu   Arg
                        340                           345                             350

CTC   GCC   TCA   GGC   AAG   AGG   TTG   CTA   ACC   CCA   GAC   GAG   GTT   TAT   CAA   GTA       1344
Leu   Ala   Ser   Gly   Lys   Arg   Leu   Leu   Thr   Pro   Asp   Glu   Val   Tyr   Gln   Val
                  355                           360                             365

ATT   ACC   TCT   ACG   GCT   AAG   GAT   ATC   GGC   CCG   CCC   GGT   TTT   GAC   GTC   TTT       1392
Ile   Thr   Ser   Thr   Ala   Lys   Asp   Ile   Gly   Pro   Pro   Gly   Phe   Asp   Val   Phe
            370                           375                             380

TCG   GGC   TAC   GGC   TTA   GTT   GAC   GCA   TAC   GCC   GCA   GTT   GTG   GCC   GCG   CTA       1440
Ser   Gly   Tyr   Gly   Leu   Val   Asp   Ala   Tyr   Ala   Ala   Val   Val   Ala   Ala   Leu
      385                           390                             395

AGT   CGC   TAACTTTTTA   TATAGAATTC   AAATTGAGTA   TATGCCCACG   TGGACTGAGT                          1496
Ser   Arg
400

ACATACTCTA   TAAAAAATTG   GCGAAAACTC   CGTCGCCAGG   TGACGTCGTT   GAAATAGTTC                          1556

CAGATCTCGT   CGGCTTTCAC   GACTTGACGG   GGTACCACGT   CCTTGAGGTG   TTGGAAAGCA                          1616

TGGGCAAAGT   GGAGGTGTTT   GACAGGGAGA   GAGTCGTTGT   TGCGTTTGAT   CACTTGTCCC                          1676

CGCCCCCAAA   TCAGAGAGCC   GCTGAGATAA   TGGTGTACAT   AAGGCGTCAT   GTCAAGGCTC                          1736

TGGGCTTCCT   AATTTCTACG   ACGTAGGCGC   GGCATTTTGC   ACCAGATTAT   CTGGAGAAAT                          1796

ACGCCTTGCC   GGGCCAAGTG   ATCTTCGCCG   CGATAGCCAC   ACTTTCACCG   CC                                  1848
```

( 2 ) INFORMATION FOR SEQ ID NO:2:

( i ) SEQUENCE CHARACTERISTICS:
        ( A ) LENGTH: 401 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met   Ser   Gln   Tyr   Leu   Lys   Arg   Arg   Lys   Lys   Leu   Ala   Gln   Cys   Gln   Arg
 1                      5                           10                            15

Phe   Gly   Gly   Thr   Ser   Gly   Ile   Ser   Ser   Ser   Arg   Glu   Ile   Val   Gly
                  20                          25                            30

Tyr   Val   Asp   Ser   Pro   Pro   Ser   Glu   Ala   Leu   Lys   Glu   Leu   Asn   Lys   Thr
            35                          40                            45

Gly   Asp   Ile   Lys   Ile   Ile   Lys   His   Leu   Lys   Glu   Ile   Lys   Ala   Ile   Val
```

```
                  50                         55                         60
Leu   Asn   Ile   Pro   Asp   Asn   Lys   Thr   Glu   Lys   Leu   Lys   Glu   Lys   Leu   Lys
65                        70                        75                              80

Gly   Val   Arg   Tyr   Ile   Glu   Glu   Asp   Gly   Val   Ala   Tyr   Gly   Phe   Gly   Phe
                  85                        90                              95

Ser   Asn   Tyr   Thr   Asp   Val   Gln   Trp   Asn   Val   Lys   Met   Ile   Asn   Ala   Pro
                  100                       105                       110

Arg   Leu   Gly   Arg   Leu   Phe   Ser   His   Ile   Trp   Arg   Arg   Ala   Phe   Gly   Tyr
            115                             120                       125

Gly   Val   Lys   Val   Ala   Val   Leu   Asp   Thr   Gly   Ile   Asp   Tyr   Lys   His   Pro
      130                             135                       140

Glu   Leu   Ser   Gly   Lys   Val   Val   Tyr   Cys   Ile   Asn   Thr   Leu   Gly   Asn   Thr
145                             150                       155                             160

Leu   Tyr   Lys   Gly   Thr   Asn   Leu   Arg   Lys   Cys   Ala   Asp   Arg   Lys   Cys   His
                        165                       170                       175

Gly   Thr   His   Val   Ala   Gly   Ile   Ile   Ala   Ala   Ser   Leu   Asn   Asn   Val   Ser
                  180                             185                       190

Ala   Ala   Gly   Val   Val   Pro   Lys   Val   Gln   Leu   Ile   Ala   Val   Lys   Val   Leu
            195                       200                             205

Tyr   Asp   Ser   Gly   Trp   Gly   Tyr   Tyr   Ser   Asp   Ile   Ala   Glu   Gly   Ile   Ile
      210                             215                       220

Glu   Ala   Val   Lys   Ala   Gly   Ala   Leu   Ile   Leu   Ser   Met   Ser   Leu   Gly   Gly
225                             230                       235                             240

Pro   Thr   Asp   Ala   Ser   Val   Leu   Arg   Asp   Ala   Ser   Tyr   Trp   Ala   Tyr   Gln
                        245                       250                       255

Gln   Gly   Ala   Val   Gln   Ile   Ala   Ala   Ala   Gly   Asn   Ser   Gly   Asp   Gly   Asp
                  260                             265                       270

Pro   Leu   Thr   Asn   Asn   Val   Gly   Tyr   Pro   Ala   Lys   Tyr   Ser   Cys   Val   Ile
            275                       280                       285

Ala   Ala   Ala   Ala   Val   Asp   Gln   Asn   Gly   Ser   Val   Pro   Thr   Trp   Ser   Ser
290                             295                       300

Asp   Gly   Pro   Glu   Val   Asp   Thr   Ala   Ala   Pro   Gly   Val   Asn   Ile   Leu   Ser
305                       310                       315                             320

Thr   Tyr   Pro   Gly   Gly   Arg   Tyr   Ala   Tyr   Met   Ser   Gly   Thr   Ser   Met   Ala
                        325                       330                       335

Thr   Pro   His   Val   Thr   Gly   Val   Ala   Ala   Leu   Ile   Gln   Ala   Leu   Arg   Leu
                  340                       345                       350

Ala   Ser   Gly   Lys   Arg   Leu   Leu   Thr   Pro   Asp   Glu   Val   Tyr   Gln   Val   Ile
            355                       360                       365

Thr   Ser   Thr   Ala   Lys   Asp   Ile   Gly   Pro   Pro   Gly   Phe   Asp   Val   Phe   Ser
370                             375                       380

Gly   Tyr   Gly   Leu   Val   Asp   Ala   Tyr   Ala   Ala   Val   Val   Ala   Ala   Leu   Ser
385                       390                       395                             400

Arg
```

( 2 ) INFORMATION FOR SEQ ID NO:3:

( i ) SEQUENCE CHARACTERISTICS:
        ( A ) LENGTH: 318 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

-continued

```
Tyr  Ile  Glu  Glu  Asp  Gly  Val  Ala  Tyr  Ala  Phe  Gly  Phe  Ser  Asn  Tyr
1              5                        10                       15

Thr  Asp  Val  Gln  Trp  Asn  Val  Lys  Met  Ile  Asn  Ala  Pro  Arg  Leu  Gly
               20                  25                       30

Arg  Leu  Phe  Ser  His  Ile  Trp  Arg  Arg  Ala  Phe  Gly  Tyr  Gly  Val  Lys
          35                       40                       45

Val  Ala  Val  Leu  Asp  Thr  Gly  Ile  Asp  Tyr  Lys  His  Pro  Glu  Leu  Ser
     50                       55                  60

Gly  Lys  Val  Val  Tyr  Cys  Ile  Asn  Thr  Leu  Gly  Asn  Thr  Leu  Tyr  Lys
65                       70                  75                            80

Gly  Thr  Asn  Leu  Arg  Lys  Cys  Ala  Asp  Arg  Lys  Cys  His  Gly  Thr  His
               85                       90                            95

Val  Ala  Gly  Ile  Ile  Ala  Ala  Ser  Leu  Asn  Asn  Val  Ser  Ala  Ala  Gly
          100                       105                      110

Val  Val  Pro  Lys  Val  Gln  Leu  Ile  Ala  Val  Lys  Val  Leu  Tyr  Asp  Ser
          115                       120                      125

Gly  Ser  Gly  Tyr  Tyr  Ser  Asp  Ile  Ala  Glu  Gly  Ile  Ile  Glu  Ala  Val
     130                  135                      140

Lys  Ala  Gly  Ala  Leu  Ile  Leu  Ser  Met  Ser  Leu  Gly  Gly  Pro  Thr  Asp
145                       150                      155                      160

Ala  Ser  Val  Leu  Arg  Asp  Ala  Ser  Thr  Trp  Ala  Tyr  Gln  Gln  Gly  Ala
               165                       170                      175

Val  Gln  Ile  Ala  Ala  Ala  Gly  Asn  Ser  Gly  Asp  Gly  Asp  Pro  Leu  Thr
          180                       185                      190

Asn  Asn  Val  Gly  Tyr  Pro  Ala  Lys  Thr  Ser  Cys  Val  Ile  Ala  Ala  Ala
          195                       200                      205

Ala  Val  Asp  Gln  Asn  Gly  Ser  Val  Pro  Thr  Trp  Ser  Ser  Asp  Gly  Pro
     210                       215                 220

Glu  Val  Asp  Thr  Ala  Ala  Pro  Gly  Val  Asn  Ile  Leu  Ser  Thr  Tyr  Pro
225                       230                 235                           240

Gly  Gly  Arg  Tyr  Ala  Tyr  Met  Ser  Gly  Thr  Ser  Met  Ala  Thr  Pro  His
                    245                      250                      255

Val  Thr  Gly  Val  Ala  Ala  Leu  Ile  Gln  Ala  Leu  Arg  Leu  Ala  Ser  Gly
               260                      265                 270

Lys  Arg  Leu  Leu  Thr  Pro  Asp  Glu  Val  Tyr  Gln  Val  Ile  Thr  Ser  Thr
          275                      280                      285

Ala  Lys  Asp  Ile  Gly  Pro  Pro  Gly  Phe  Asp  Val  Phe  Ser  Gly  Tyr  Gly
     290                      295                      300

Leu  Val  Asp  Ala  Tyr  Ala  Ala  Val  Val  Ala  Ala  Leu  Ser  Arg
305                      310                      315
```